quot;US007718357B2

(12) United States Patent
Guy et al.

(10) Patent No.: US 7,718,357 B2
(45) Date of Patent: May 18, 2010

(54) METHOD OF IMMUNIZATION AGAINST THE 4 DENGUE SEROTYPES

(75) Inventors: Bruno Guy, Lyons (FR); Véronique Barban, Craponne (FR); Rémi Forrat, Serezin du Rhone (FR); Jean Lang, Moins (FR)

(73) Assignee: Sanofi Pasteur SA, Lyons (FR)

( * ) Notice: Subject to any disclaimer, the term of this patent is extended or adjusted under 35 U.S.C. 154(b) by 0 days.

(21) Appl. No.: 11/776,816

(22) Filed: Jul. 12, 2007

(65) Prior Publication Data

US 2008/0014219 A1     Jan. 17, 2008

Related U.S. Application Data

(60) Provisional application No. 60/829,361, filed on Oct. 13, 2006.

(30) Foreign Application Priority Data

Jul. 12, 2006     (FR)     .................................. 06 06324

(51) Int. Cl.
    *C12Q 1/70*     (2006.01)
    *A61K 39/12*     (2006.01)
(52) U.S. Cl. ...................... 435/5; 424/201.1; 424/218.1
(58) Field of Classification Search ........................ None
    See application file for complete search history.

(56) References Cited

U.S. PATENT DOCUMENTS

| 6,638,514 | B1 | 10/2003 | Eckels et al. |
| 2004/0192631 | A1 | 9/2004 | Xiang et al. |
| 2004/0259224 | A1 | 12/2004 | Guirakhoo |
| 2008/0085288 | A1 | 4/2008 | Guy et al. |
| 2008/0131460 | A1 | 6/2008 | Guy et al. |

FOREIGN PATENT DOCUMENTS

| EP | 1159968 | 12/2001 |
| WO | 99/61916 | 12/1999 |
| WO | 00/57910 | 10/2000 |
| WO | 01/21811 | 3/2001 |
| WO | 01/91790 | 12/2001 |
| WO | 03/101397 | 12/2003 |
| WO | 01/60847 A1 | 8/2007 |

OTHER PUBLICATIONS

Whitehead et al. Nature Review Microbiology, Jul. 2007, 5:519-528.*
Shresta et al. J. Virology, Oct. 2006, 80(20):10208-10217.*

Guirakhoo et al., "Safety and Efficacy of Chimeric Yellow Fever-Dengue Virus Tetravalent Vaccine Formulations in Nonhuman Primates," Journal of Virology, 4761-4775 (2004).
Halstead et al., "Studes on the Immunization of Monkeys Against Dengue II. Protection Following Inoculation of Combinations of Viruses," The American Journal of Tropical Medicine and Hygiene, 22(3):375-381 (1973).
Zhou et al., "Sculpting the immunological response to dengue fever by polytopic vaccination," Vaccine, 24:2451-2459 (2006).
Rothman et al., "Induction of T lymphocyte responses to dengue virus by a candidate tetravalent live attenuated dengue virus vaccine," Vaccine (19):4694-4699 (2001).
Bhamarapravati et al., "Live attenuated tetravalent dengue vaccine," Vaccine (18):44-47 (2000).
Halstead et al., "Studies on the Immunization of Monkeys Against Dengue I. Protection Derived from Single and Sequential Virus Infections," The American Journal of Tropical Medicine and Hygiene, 22(3):365-374 (1973).
Guirakhoo et al., "Construction Safety and Immunogenicity non-human of a chimeric yellow fever-dengue virus tetravalent vaccine", Journal of Virology—The American Society for Microbiology, 2001, 75(16), 7290-7304.
Blaney, J. E., "Development of a live attenuated dengue virus vaccine using reverse genetics", Viral Immunology, 2006, 19(1), 10-32.
Sabchareon et al., "Safety and Immunogenecity of tetravalent live-attenuated dengue vaccines in Thai adult volunteers" Role of serotype concentration ratio and multiple doses, American Journal of Tropical Medicine and Hygiene, 2002, 66(3), 264-272.
Guirakhoo et al., "Viremia and Immunogenicity in Nonhuman Primates of a Tetravalent Yellow Fever Dengue Chimeric Vaccine Genetic Reconstructions, Dose Adjustment and Antibody Responses Against Wild-Type Dengue Virus Isolates", Virology, 2002, 298(1), 146-159.
Halstead, S.B. et al.: Protection Derived from Single Sequential Virus Infections, Journal of Tropical Medicine & Hygiene, 1973, pp. 365-374, vol. 22, No. 3.
Non-Final Office Action issued for U.S. Appl. No. 11/944,311, mailed on Jun. 15, 2009.
Final Office Action issued for U.S. Appl. No. 11/866,382, mailed on Jun. 15, 2009.

* cited by examiner

*Primary Examiner*—Stacy B Chen
(74) *Attorney, Agent, or Firm*—McDonnell Boehnen Hulbert & Berghoff LLP

(57) ABSTRACT

The invention relates to a method for inducing a homologous protection against the 4 dengue serotypes in a patient, comprising the sequential administration, to said patient, (i) of a dose of a vaccinal dengue virus of a first serotype and of a dose of a vaccinal dengue virus of a second serotype, and (ii) of a dose of a vaccinal dengue virus of a third serotype and of a dose of a vaccinal dengue virus of a fourth serotype, in which the vaccinal dengue viruses (ii) are administered at least 30 days and at most 1 year after administration of the vaccinal viruses (i).

13 Claims, No Drawings

METHOD OF IMMUNIZATION AGAINST THE 4 DENGUE SEROTYPES

This application claims priority to and incorporates by reference U.S. provisional patent application No. 60/829,361 filed Oct. 13, 2006, and French patent application number FR 06 06324 filed on Jul. 12, 2006.

BACKGROUND OF THE INVENTION

1. Field of the Invention

The invention relates to a method for inducing a homologous protection against the 4 dengue serotypes in a patient, comprising the sequential administration, to said patient, (i) of a dose of a vaccinal dengue virus of a first serotype and of a dose of a vaccinal dengue virus of a second serotype, and (ii) of a dose of a vaccinal dengue virus of a third serotype and of a dose of a vaccinal dengue virus of a fourth serotype, in which the vaccinal dengue viruses (ii) are administered at least 30 days and at most 1 year after administration of the vaccinal dengue viruses (i).

2. Summary of the Related Art

Dengue diseases are caused by four viruses of the flavivirus genus, of the serological type, which are similar but distinct from an antigenic point of view (Gübler et al., 1988 In: Epidemiology of arthropod-borne viral disease. Monath TPM, editor, Boca Raton (Fla.): CRC Press: 223-60; Kautner et al., 1997, J. of Pediatrics, 131:516-524; Rigau-Pérez et al., 1998, Lancet; 352: 971-977; Vaughn et al., 1997, J Infect Dis; 176: 322-30). Infection with a dengue serotype can produce a clinical disease spectrum ranging from a nonspecific viral syndrome to a severe hemorrhagic disease which is fatal. The incubation period of dengue fever after a mosquito bite is approximately 4 days (ranging from 3 to 14 days). Dengue fever is characterized by a biphasic fever, headaches, pain in various parts of the body, prostration, eruptions, lymphadenopathy and leukopenia (Kautner et al., 1997, J. of Pediatrics, 131:516-524; Rigau-Pérez et al., 1998, Lancet; 352: 971-977). The viremia period is the same as for febrile diseases (Vaughn et al., 1997, J. Infect. Dis.; 176: 322-30). Recovery from dengue fever occurs after 7 to 10 days, but there is usually a prolonged asthenia. Decreases in leukocyte and platelet count are common.

Hemorrhagic dengue is a severe febrile disease characterized by anomalies in homeostasis and an increase in vascular permeability which can result in hypovolemia and in hypotension (dengue with shock syndrome) often complicated by severe internal hemorrhaging. The mortality rate of hemorrhagic dengue can be up to 10% without treatment, but is 1% in most centers with experience in treatment (WHO technical Guide, 1986. Dengue haemorrhagic fever: diagnosis, treatment and control, p1 -2. World Health Organization, Geneva, Switzerland).

The routine laboratory diagnosis of dengue is based on isolation of the virus and/or detection of antibodies specific for the dengue virus.

Dengue is the second most common tropical infectious disease after malaria, more than half the world's population (2.5 billion) living in regions where there is a risk of epidemic transmission. Each year, cases of dengue are estimated at 50-100 million, cases of patients hospitalized for hemorrhagic dengue at 500 000, and the number of deaths at 25 000. Dengue is endemic in Asia, in the Pacific region, in Africa, in Latin America and in the Caribbean. More than 100 tropical countries are endemic for dengue virus infections and hemorrhagic dengue has been documented in 60 of these countries (Gubler, 2002, TRENDS in Microbiology. 10:100-103; Monath, 1994, Proc. Natl. Acad. Sci.; 91: 2395-2400). A certain number of well-described factors appear to be involved in dengue: population growth; unplanned and uncontrolled urbanization, in particular in combination with poverty; an increase in air travel; the lack of effective control of mosquitoes and the deterioration of hygiene infrastructures and of public health (Gubler, 2002, TRENDS in Microbiology. 10: 100-103). Individuals who travel and expatriates are increasingly warned about dengue (Shirtcliffe et al., 1998, J. Roy. Coll. Phys. Lond.; 32: 235-237). Dengue has constituted one of the main causes of febrile diseases in American troops during deployments in tropical zones endemic for dengue (DeFraites et al., 1994, MMWR 1994; 43: 845-848).

The viruses are maintained in a cycle which involves humans and *Aedes aegypti*, a domestic mosquito which bites during the day, and which prefers to feed off humans. The infection in humans is initiated by injection of the virus while an infected *Aedes aegypti* mosquito feeds on the blood. The virus in the saliva is deposited mainly in the extravascular tissues. The first category of cells infected after inoculation are dendritic cells, which then migrate to the lymph nodes (Wu et al., 2000, Nature Med.; 7:816-820). After an initial replication in the skin and in the lymph nodes, the virus appears in the blood during the acute febrile phase, generally for 3 to 5 days.

Monocytes and macrophages are, with dendritic cells, among the first targets of the dengue virus. Protection against a homotypic reinfection is complete and probably lasts for a lifetime, but crossprotection between the various dengue types lasts less than a few weeks to a few months (Sabin, 1952, Am. J. Trop. Med. Hyg.; 1: 30-50). Consequently, an individual can experience an infection with a different serotype. A second infection with dengue is in theory a risk factor for developing a severe dengue disease. However, hemorrhagic dengue is multifactorial: these factors include the strain of the virus involved, and also the age, the immune status and the genetic predisposition of the patient. Two factors play a major role in the occurrence of hemorrhagic dengue: rapid viral replication with a high viremia (the severity of the disease being associated with the level of viremia; Vaughn et al., 2000, J. Inf. Dis.; 181: 2-9) and a substantially inflammatory response with the release of high levels of inflammatory mediators (Rothman and Ennis, 1999, Virology; 257: 1-6). There is no specific treatment against dengue. The treatment for dengue fever is symptomatic with confinement to bed, control of the fever and of the pain with antipyretics and analgesics, and adequate fluid intake. The treatment for hemorrhagic dengue requires equilibration of fluid losses, replacement of clotting factors and heparin infusion.

Preventive measures are currently based on controlling the vector and taking personal protection steps which are difficult to implement and expensive. No vaccine against dengue has been approved at this time. Given that the four dengue serotypes are in circulation in the world and since they have been reported as being involved in cases of dengue hemorrhagic fever, immunization should ideally confer protection against the four serotypes of the dengue virus.

Sequential immunization strategies have previously been implemented with the aim of inducing a heterologous protection among the various dengue serotypes.

Thus, Price (1968, Am. J. Epid., 88:392-397) has described a method of sequential immunization against dengue comprising a series of two infections with dengue serotype 1 and then with dengue serotype 2, which conferred protection in a challenge test with dengue serotype 3 or 4.

Whitehead et al. (1970, Am. J. Trop. Med. Hyg., 19:94-102) sought to determine the influence of a sequential monovalent infection with two or three of the four dengue serotypes, on the conferred heterologous immunity. Gibbons were thus initially infected with a dengue virus serotype 1, 2, 3 or 4. Following a second infection with a heterologous serotype, a variable viremia was detected which was dependent on the sequence of infection and in particular on the serotype used for the first infection. More specifically, a second viremia appeared in gibbons initially infected with serotype 2, 3 or 4 and then challenged with serotype 1, 2 or 4.

Scherer et al. (1972, Am. J. Epid., 95:67-79) described a sequential monovalent infection comprising a first infection with one of the four dengue serotypes, followed by a second infection, or even a third infection, with a homologous or heterologous serotype. The proposed schemes did not make it possible to obtain a satisfactory protection against a challenge with a heterologous serotype.

Halstead et al. (1973, Am. J. Trop. Med. Hyg., 22:365-374) evaluated, in monkeys, a method of sequential immunization against dengue comprising a series of two, three or four monovalent infections with heterologous dengue serotypes 1 to 4. The authors concluded that a protection against a subsequent infection could be obtained with the immunization sequence consisting of serotypes 1, 2 then 4, followed by a challenge with serotype 3. Bivalent immunization is neither described nor suggested. Furthermore, the authors advise against sequential immunizations due to their laborious nature and to the random nature of the results generated.

Halstead et al. (1973, Am. J. Trop. Med. Hyg., 22:375-381) also found that a bivalent immunization with two heterologous dengue serotypes did not protect, or only partially protected, against an infection with a third dengue serotype.

SUMMARY OF THE INVENTION

In the context of the present invention, the objective is to induce a homologous protection against the 4 dengue serotypes. The inventors demonstrated that it is possible to generate an immune response comprising antibodies which neutralize the 4 serotypes when the latter are administered sequentially in pairs.

The inventors have in particular shown that a DEN-1,2 bivalent immunization followed two months later by a DEN-3,4 bivalent immunization induces high responses against the four serotypes in all the monkeys immunized. The immune response thus generated is quantitatively and qualitatively greater (covers all the serotypes).

DETAILED DESCRIPTION OF THE INVENTION

According to a first subject, the present invention therefore relates to vaccinal compositions comprising (i) a dose of a vaccinal dengue virus of a first serotype and a dose of a vaccinal dengue virus of a second serotype, and (ii) a dose of a vaccinal dengue virus of a third serotype and a dose of a vaccinal dengue virus of a fourth serotype, as a combination vaccinal composition against dengue for sequential administration, in which the vaccinal dengue viruses (ii) are administered at least 30 days and at most 1 year after the administration of the vaccinal dengue viruses (i).

According to one embodiment of the vaccinal compositions according to the invention, the vaccinal viruses (ii) are administered 30 days to 3 months after the administration of the vaccinal viruses (i).

According to another specific embodiment of the vaccinal compositions according to the invention, the vaccinal viruses (ii) are administered 30 days after the administration of the vaccinal viruses (i).

According to another embodiment of the vaccinal compositions according to the invention, the vaccinal dengue viruses (i) are administered in the form of a bivalent vaccinal composition.

According to another embodiment of the vaccinal compositions according to the invention, the vaccinal dengue viruses (ii) are administered in the form of a bivalent vaccinal composition.

According to one specific embodiment of the vaccinal compositions according to the invention, said vaccinal dengue virus serotype 1 is selected from the group consisting of the VDV1 strain and of a Chimerivax™ DEN-1.

According to another specific embodiment of the vaccinal compositions according to the invention, said vaccinal dengue virus serotype 2 is selected from the group consisting of the VDV2 strain and of a Chimerivax™ DEN-2.

According to another specific embodiment of the vaccinal compositions according to the invention, said vaccinal dengue virus serotype 1 is the VDV1 strain and said vaccinal dengue virus serotype 2 is the VDV2 strain.

According to another specific embodiment of the vaccinal compositions according to the invention, said vaccinal dengue virus serotype 1 is a Chimerivax™ DEN-1 and said vaccinal dengue virus serotype 2 is a Chimerivax™ DEN-2.

According to another specific embodiment of the vaccinal compositions according to the invention, said vaccinal dengue virus serotype 3 is a Chimerivax™ DEN-3.

According to another specific embodiment of the vaccinal compositions according to the invention, said vaccinal dengue virus serotype 4 is a Chimerivax™ DEN-4.

According to another specific embodiment of the vaccinal compositions according to the invention, the first and second serotypes are, respectively, CYD DEN1 and CYD DEN2 and the third and fourth serotypes are, respectively, CYD DEN3 and CYD DEN 4.

According to another specific embodiment of the vaccinal compositions according to the invention, the doses of vaccinal dengue viruses serotypes 1, 2, 3 and 4 are each within a range of from $10^3$ to $10^5$ $CCID_{50}$.

A subject of the invention is also the use of a vaccinal dengue virus of a third serotype and of a vaccinal dengue virus of a fourth serotype, for the manufacture of a dengue vaccine intended to be administered to a patient who has received, at least 30 days and at most 1 year beforehand, a dose of a vaccinal dengue virus of a first serotype and a dose of a vaccinal dengue virus of a second serotype.

According to another specific embodiment of the use according to the invention, the third and fourth serotypes are administered in the form of a bivalent vaccinal composition.

According to another specific embodiment of the use according to the invention, the first and second serotypes are administered in the form of a bivalent vaccinal composition.

According to another specific embodiment of the use according to the invention, said vaccinal dengue virus serotype 1 is selected from the group consisting of the VDV1 strain and a Chimerivax™ DEN-1.

According to another specific embodiment of the use according to the invention, said vaccinal dengue virus serotype 2 is selected from the group consisting of the VDV2 strain and a Chimerivax™ DEN-2.

According to another specific embodiment of the use according to the invention, said vaccinal dengue virus serotype 1 is the VDV1 strain and said vaccinal dengue virus serotype 2 is the VDV2 strain.

According to another specific embodiment of the use according to the invention, said vaccinal dengue virus serotype 1 is a Chimerivax™ DEN-1 and said vaccinal dengue virus serotype 2 is a Chimerivax™ DEN-2.

According to another specific embodiment of the use according to the invention, said vaccinal dengue virus serotype 3 is a Chimerivax™ DEN-3.

According to another specific embodiment of the use according to the invention, said vaccinal dengue virus serotype 4 is a Chimerivax™ DEN-4.

According to another specific embodiment of the use according to the invention, the first and second serotypes are, respectively, CYD DEN1 and CYD DEN2 and the third and fourth serotypes are, respectively, CYD DEN3 and CYD DEN4.

According to another specific embodiment of the use according to the invention, the third and fourth serotypes are administered 30 days to 3 months after the administration of the first and second serotypes.

According to another specific embodiment of the use according to the invention, the third and fourth serotypes are administered 30 days after the administration of the first and second serotypes.

According to another specific embodiment of the use according to the invention, the doses of vaccinal dengue viruses serotypes 1, 2, 3 and 4 are each within a range of from $10^3$ to $10^5$ $CCID_{50}$.

According to another aspect, the invention comprises a vaccinal dengue virus kit comprising four different vaccinal dengue virus serotypes, wherein
a) each vaccinal dengue virus serotype is in a separate dosage form;
b) two of the four vaccinal dengue virus serotypes are combined in a single dosage form; or
c) two of the four vaccinal dengue virus serotypes are combined in a first dosage form and the other two of the four dengue virus serotypes are combined in a second dosage form.

Preferably, the vaccinal dengue viruses serotypes are each present in the dosage forms in a range of from $10^3$ to $10^5$ $CCID_{50}$.

Also preferably, the vaccinal dengue virus kit comprises two dosage forms, wherein two of the four serotypes are combined in a first dosage form and the other two of the four serotypes are combined in a second dosage form.

In some embodiments of this aspect of the invention, one of the vaccinal dengue virus serotypes is selected from the group consisting of the VDV1 strain and of a CYD DEN-1.

In some embodiments of this aspect of the invention, one of the vaccinal dengue virus serotypes is selected from the group consisting of the VDV2 strain and of a CYD DEN-2.

In some embodiments of this aspect of the invention, one of the vaccinal dengue virus serotypes is the VDV1 strain and another vaccinal dengue virus serotype is the VDV2 strain.

In some embodiments of this aspect of the invention, one of the vaccinal dengue virus serotypes is CYD DEN-1 and another vaccinal dengue virus serotype is CYD DEN-2 strain.

In some embodiments of this aspect of the invention, one of the vaccinal dengue virus serotypes is a CYD DEN-3.

In some embodiments of this aspect of the invention, one of the vaccinal dengue virus serotypes is a CYD DEN-4.

In one embodiment of this aspect of the invention, the dengue virus kit comprises the vaccinal dengue viruses CYD DEN1, CYD DEN2, CYD DEN3, and CYD DEN4, wherein each of the CYD DEN1 and CYD DEN2 serotypes are in a dosage form where each is the only dengue virus serotype in the dosage form or the two are combined together in a single dosage form, and wherein each of the CYD DEN3 and CYD DEN4 serotypes are in a dosage form where each is the only dengue virus serotype in the dosage form or the two are combined together in a single dosage form.

According to another aspect, the invention comprises a kit comprising two different vaccinal dengue virus serotypes, wherein
a) each vaccinal dengue virus serotype is in a separate dosage form; or
b) both vaccinal dengue virus serotypes are combined in a single dosage form.

Preferably in this aspect of the invention, the vaccinal dengue viruses serotypes are each present in the dosage forms in a range of from $10^3$ to $10^5$ $CCID_{50}$.

Also preferably in this aspect of the invention, the two serotypes are combined in a single dosage form.

In some embodiments of this aspect of the invention, one of the vaccinal dengue virus serotypes is selected from the group consisting of the VDV1 strain and of a CYD DEN-1.

In some embodiments of this aspect of the invention, one of the vaccinal dengue virus serotypes is selected from the group consisting of the VDV2 strain and of a CYD DEN-2.

In some embodiments of this aspect of the invention, one of the vaccinal dengue virus serotypes is the VDV1 strain and the other vaccinal dengue virus serotype is the VDV2 strain.

In some embodiments of this aspect of the invention, one of the vaccinal dengue virus serotypes is CYD DEN-1 and the other vaccinal dengue virus serotype is CYD DEN-2 strain.

In some embodiments of this aspect of the invention, one of the vaccinal dengue virus serotypes is a CYD DEN-3.

In some embodiments of this aspect of the invention, one of the vaccinal dengue virus serotypes is a CYD DEN-4.

In another aspect, the invention comprises a method of preventing or inhibiting a dengue virus infection comprising:
a) in a first administration administering to a subject an effective amount of a first and second vaccinal dengue virus serotype; and
b) in a second administration administering to the subject an effective amount of a third and fourth vaccinal dengue virus serotype
wherein
i) the first, second, third, and fourth vaccinal dengue virus serotypes are each different one from another;
ii) the second administration occurs from about 30 days to about 1 year after the first administration;
iii) each vaccinal dengue virus serotypes is administered in an amount that is sufficient to induce a homologous immune response;
iv) the first and second serotypes are administered in separate dosages forms or together in a single dosage form; and
v) the third and fourth serotypes are administered in separate dosages forms or together in a single dosage form.

In some embodiments of this aspect of the invention, the third and fourth serotypes are administered in a single dosage form.

In some embodiments of this aspect of the invention, the first and second serotypes are administered in a single dosage form.

In some embodiments of this aspect of the invention, the first or second vaccinal dengue virus serotype is selected from the group consisting of the VDV1 strain and of a CYD DEN-1.

In some embodiments of this aspect of the invention, the first or second vaccinal dengue virus serotype is selected from the group consisting of the VDV2 strain and of a CYD DEN-2.

In some embodiments of this aspect of the invention, the first vaccinal dengue virus serotype is the VDV1 strain and the second vaccinal dengue virus serotype is the VDV2 strain.

In some embodiments of this aspect of the invention, the first vaccinal dengue virus serotype is a CYD DEN-1 and the second vaccinal dengue virus serotype 2 is a CYD DEN-2.

In some embodiments of this aspect of the invention, the third vaccinal dengue virus serotype is a CYD DEN-3.

In some embodiments of this aspect of the invention, the fourth vaccinal dengue virus serotype 4 is a CYD DEN-4.

In some embodiments of this aspect of the invention, first and second serotypes are CYD DEN1 and CYD DEN2 and the third and fourth serotypes are CYD DEN3 and CYD DEN4.

In some embodiments of this aspect of the invention, the third and fourth serotypes are administered 30 days to 3 months after the administration of the first and second serotypes.

In some embodiments of this aspect of the invention, the third and fourth serotypes are administered 30 days after the administration of the first and second serotypes.

In some embodiments of this aspect of the invention, the dosage forms comprise the vaccinal dengue viruses serotypes in a range of from $10^3$ to $10^5$ $CCID_{50}$.

The invention will be described in further detail in the description which follows.

Definitions

"Dengue viruses" or "DENs" are positive, single-stranded RNA viruses belonging to the *Flavivirus* genus of the flaviviridae family. The genomic RNA contains a type I cap at the 5' end but lacks a poly-A tail at the 3' end. The genomic organization consists of the following elements: 5' noncoding region (NCR), structural proteins (capsid (C), premembrane/membrane (prM/M), envelope (E)) and nonstructural proteins (NS1-NS2A-NS2B-NS3-NS4A-NS4B-NS5), and 3' NCR. The genomic viral RNA is associated with the capsid proteins so as to form a nucleocapsid. As for the other *flaviviruses*, the DEN viral genome encodes an uninterrupted coding region which is translated into a single polyprotein.

"VDV" or "Vero dengue vaccine" denotes a live attenuated dengue viral strain adapted on Vero cells and capable of inducing a specific humoral response, including the induction of neutralizing antibodies, in primates and in particular in humans.

"VDV-1" is a strain obtained from a wild-type strain DEN-1 16007 which was subjected to 11 passages on PDK cells (DEN-1 16007/PDK11), which was then amplified on Vero cells at 32° C., and the RNA of which was purified and transfected into Vero cells. The VDV-1 strain has 14 additional mutations compared to the vaccinal strain DEN-1 16007/PDK13 (13 passages on PDK—Primary Dog Kidney—cells). The DEN-1 16007/PDK13 strain, also called "LAV1", was described in patent application EP1159968 in the name of Mahidol University and was deposited with the Collection Nationale de Cultures de Microorganismes (CNCM) [National Collection of Microorganism Cultures] under the number 1-2480. The complete sequence of the VDV-1 strain is given in the sequence SEQ ID NO: 1. Said strain can be readily reproduced from said sequence. A method of preparation and the characterization of the VDV-1 strain have been described in the International patent application filed under the names of Sanofi-Pasteur and of the Center for Disease Control and Prevention under the number PCT/IB 2006/001313.

"VDV-2" is a strain obtained from a wild-type strain DEN-2 16681 which was subjected to 50 passages on PDK cells (DEN-2 16681/PDK50), and plaque-purified, and the RNA of which was extracted and purified before being transfected into Vero cells. The VDV-2 strain was then obtained by plaque-purification and amplification on Vero cells. The VDV-2 strain has 10 additional mutations compared with the vaccinal strain DEN-2 16681 /PDK53 (53 passages on PDK cells), 4 mutations of which are silent. The DEN-2 16681/PDK53 strain, also called "LAV2", was described in patent application EP1 159968 in the name of Mahidol University and was deposited with the Collection Nationale de Cultures de Microorganismes (CNCM) under the number I-2481. The complete sequence of the VDV-2 strain is shown in the sequence SEQ ID NO:2. The VDV-2 strain can be readily reproduced from said sequence. A method of preparation and of characterization of the VDV-2 strain has been described in the International patent application filed in the names of Sanofi-Pasteur and of the Center for Disease Control and Prevention under the number PCT/IB 2006/001513.

As used herein the terms "ChimeriVax™ dengue" and "CYD" are equivalent and denote a chimeric yellow fever (YF) virus which comprises the backbone of a YF virus in which the sequences encoding the premembrane and envelope proteins have been replaced with those of a DEN virus. The term "CYD-1 or CYD DEN1" is thus used to describe a chimeric YF virus containing the prM and E sequences of a dengue serotype 1 strain (DEN-1). The term "CYD-2 or CYD DEN2" is used to describe a chimeric YF virus containing the prM and E sequences of a DEN-2 strain. The term "CYD-3 or CYD DEN3" is used to describe a chimeric YF virus containing the prM and E sequences of a DEN-3 strain. The term "CYD-4 or CYD DEN4" is used to describe a chimeric YF virus containing the prM and E sequences of a DEN-4 strain. The preparation of these ChimeriVax™ or CYD dengues has been described in detail in International patent applications WO 98/37911 and WO 03/101397, to which reference may be made for a precise description of the method for preparing them. The chimeras described in the examples were generated using the prM and E sequences derived from the DEN1 PUO359, DEN2 PR 159, DEN3 PaH881 and DEN4 TVP 980 strains. Any strain of the dengue virus could be used in the context of the present invention for the construction of the chimeras.

Preferably, the chimeric YF virus comprises the backbone of an attenuated yellow fever strain YF17D (Theiler M, and Smith H H (1937) J Exp. Med 65, p 767-786.) (YF17D/DEN-1, YF17D/DEN-2, YF17D/DEN-3, YF17D/DEN-4 virus). Examples of YF17D strains which can be used include YF17D204 (YF-Vax®, Sanofi-Pasteur, Swifwater, Pa., USA; Stamaril®, Sanofi-Pasteur, Marcy l'Etoile, France; ARIL-VAX™, Chiron, Speke, Liverpool, UK; FLAVIMUN®, Berna Biotech, Bern, Switzerland); YF17D-204 France (X15067,X15062); YF17D-204,234 US (Rice et al., 1985, Science, 229:726-733), or else related strains YF17DD (Genbank accession number U17066), YF17D-213 (Genbank accession number U17067) and the YF17DD strains described by Galler et al. (1998, Vaccines 16(9/10):1024-1028). Any other yellow fever virus strain sufficiently attenuated for use in humans can be used.

A "monovalent" vaccine contains a single dengue virus serotype. A "bivalent" vaccine contains two different dengue virus serotypes. A "trivalent" vaccine contains three different dengue virus serotypes. A "tetravalent" vaccine contains four different dengue virus serotypes.

The term "patient" denotes an individual (child or adult) who may be infected with dengue, in particular an individual at risk of infection, such as, for example, an individual who travels in regions where dengue is present or an inhabitant of these regions.

Sequential Immunization

The inventors have shown that the administration of the 4 serotypes in the form of two sequential bivalent administrations makes it possible to obtain an effective homologous protection against the 4 serotypes. The method according to the present invention is therefore most particularly valuable in the context of an immunization strategy against dengue.

The inventors therefore propose a method for inducing a neutralizing antibody response against the 4 dengue serotypes in a patient, comprising the sequential administration, to said patient, (i) of a dose of a vaccinal dengue virus of a first serotype and of a dose of a vaccinal dengue virus of a second serotype, and (ii) of a dose of a vaccinal dengue virus of a third serotype and of a dose of a vaccinal dengue virus of a fourth serotype, in which the vaccinal dengue viruses (ii) are administered at least 30 days and at most 3 months after administration of the vaccinal dengue viruses (i). The administration of the first and second serotypes can be in separate dosages forms or a single, combined dosage form. Similarly, the administration of the third and fourth serotypes can be in separate dosages forms or a single, combined dosage forms. As used herein a "dosage form" is a composition comprising a dengue serotype together with a pharmaceutically acceptable carrier, diluent, or excipient. The pharmaceutically acceptable carrier, diluent, or excipient can be any known in the art that is suitable for combination with a vaccinal dengue virus.

The vaccinal dengue virus is intended to mean any viral form of dengue virus that is able to induce a specific homologous immune response. Preferably such vaccinal dengue virus can be used in the context of an immunization program in humans against an infection with a dengue virus.

By vaccinal dengue virus we mean an inactivated virus, an attenuated virus, as well as recombinant proteins such as the envelope proteins of the dengue virus. A vaccinal virus is "inactivated" if it is no longer able to replicate on permissive cells.

A vaccinal virus is "attenuated" if after growth at 37° C. or 39° C. on Huh-7, VERO and/or C6/C36. Such a vaccinal virus shows a maximal titer that is at least 10 times less than the maximal titer of the wild type in the same culture condition, using the same titration method.

A vaccinal virus showing a decreased growth on at least one of the 3 cell types identified above is deemed to be attenuated within the framework of the present invention.

A vaccinal virus usable in humans shows a positive benefit to risk ratio, which will generally satisfy regulatory requirements for obtaining market authorization.

A vaccinal dengue virus for use in the invention is preferably attenuated to such an extent that it does not induce the disease in humans. Advantageously, such a vaccinal virus results only in side effects that are at most of moderate intensity (i.e., medium to low, or even zero) in the majority of individuals vaccinated, while at the same time maintaining its ability to induce a homologous neutralizing antibody response.

Non-limiting example of vaccinal dengue virus to be used in the present invention include, but are not limited to, inactivated dengue virus, attenuated dengue virus such as attenuated strains VDV1, VDV2, strains described in, for example, WO 02/66621, WO 00/57904, WO 00/57908, WO 00/57909, WO00/57910, WO 02/0950075, and WO 02/102828 and chimeras.

Chimeric viruses show the attenuated features of the attenuated virus as defined above.

Any chimera virus expressing the envelope protein of a dengue virus and inducing an immune response comprising antibody neutralizing the serotype from which the protein comes from can be used in the present invention. Non-limiting examples include, for example, chimeras Chimerivax™ dengues as described, for example, in patent application WO 98/37911, and the dengue/dengue chimeras as described, for example, in patent applications WO 96/40933 and WO 01/60847.

The vaccinal dengue virus serotype 1 can, for example, be the vaccinal strain VDV1 or a Chimerivax™ DEN-1, in particular a YF17D/DEN-1 virus, or else a DEN-1 16007/PDK13 strain. The vaccinal dengue virus serotype 2 can, for example, be the vaccinal strain VDV2 or a Chimerivax™ DEN-2, in particular a YF17D/DEN-2 virus, or else a DEN-2 16681/PDK53 virus. The vaccinal dengue virus serotype 3 can be a Chimerivax™ DEN-3, in particular a YF17D/DEN-3 virus. The vaccinal dengue virus serotype 4 can be a Chimerivax™ DEN-4, in particular a YF17D/DEN-4 virus. It can also be a "LAV4" or "DEN-4 1036/PDK48" strain, i.e. a DEN-4 1036 strain attenuated by 48 passages on PDK cells. This strain was described in patent application EP1159968 in the name of Mahidol University and was deposited with the Collection Nationale de Cultures de Microorganismes (CNCM) under the number I-2483.

Each Chimerivax™ monovalent vaccinal dengue virus (serotypes 1, 2, 3 and 4) was prepared by amplification of each serotype on Vero cells. More specifically, the four viruses are produced separately on adherent Vero cells in serum-free medium. The viral harvest, clarified to remove the cell debris by filtration, is then concentrated and purified by ultrafiltration and chromatography in order to remove the DNA of the host cells. After the addition of a stabilizer, the vaccinal strains are stored in frozen or lyophilized form before use, and then reconstituted extemporaneously. The same method is applied for the four chimeras.

The VDV 1 and 2 strains are prepared by amplification on Vero cells. The viruses produced are harvested and clarified to remove the cell debris by filtration. The DNA is digested by enzymatic treatment. The impurities are eliminated by ultrafiltration. The infectious titers can be increased by means of a method of concentration. After the addition of a stabilizer, the strains are stored in a lyophilized or frozen form before use, and then reconstituted extemporaneously.

The multivalent compositions are obtained by simple mixing of the monovalent compositions.

According to the present invention, the 4 dengue serotypes can be administered in any order provided that they are administered in pairs sequentially, within a period of 30 days to 1 year, such as 30 days, 45 days, 60 days, 3 months, 6 months, 9 months and 1 year, being observed, advantageously a period of 30 days to 3 months, in particular a period of 1 to 2 months, being observed between the two series of administrations.

The method according to the present invention can therefore be implemented with the embodiments described below:
 (i) serotypes 1 and 2; (ii) serotypes 3 and 4; or
 (i) serotypes 1 and 3; (ii) serotypes 2 and 4; or
 (i) serotypes 1 and 4; (ii) serotypes 2 and 3; or
 (i) serotypes 2 and 3; (ii) serotypes 1 and 4; or
 (i) serotypes 2 and 4; (ii) serotypes 1 and 3; or
 (i) serotypes 3 and 4; (ii) serotypes 1 and 2.

According to specific embodiments the present invention therefore covers the following schemes:
- (i) CYD DEN-1 and CYD DEN-2; (ii) CYD DEN-3 and CYD DEN-4
- (i) CYD DEN-1 and CYD DEN-3; (ii) CYD DEN-2 and CYD DEN-4
- (i) CYD DEN-1 and CYD DEN-4; (ii) CYD DEN-2 and CYD DEN-3
- (i) CYD DEN-2 and CYD DEN-3; (ii) CYD DEN-1 and CYD DEN-4
- (i) CYD DEN-2 and CYD DEN-4; (ii) CYD DEN-1 and CYD DEN-3
- (i) CYD DEN-3 and CYD DEN-4; (ii) CYD DEN-1 and CYD DEN-2
- (i) VDV-1 and CYD DEN-2; (ii) CYD DEN-3 and CYD DEN-4
- (i) VDV-1 and CYD DEN-3; (ii) CYD DEN-2 and CYD DEN-4
- (i) VDV-1 and CYD DEN-4; (ii) CYD DEN-2 and CYD DEN-3
- (i) CYD DEN-2 and CYD DEN-3; (ii) VDV-1 and CYD DEN-4
- (i) CYD DEN-2 and CYD DEN-4; (ii) VDV-1 and CYD DEN-3
- (i) CYD DEN-3 and CYD DEN-4; (ii) VDV-1 and CYD DEN-2
- (i) CYD DEN-1 and VDV-2; (ii) CYD DEN-3 and CYD DEN-4
- (i) CYD DEN-1 and CYD DEN-3; (ii) VDV-2 and CYD DEN-4
- (i) CYD DEN-1 and CYD DEN-4; (ii) VDV-2 and CYD DEN-3
- (i) VDV-2 and CYD DEN-3; (ii) CYD DEN-1 and CYD DEN-4
- (i) VDV-2 and CYD DEN-4; (ii) CYD DEN-1 and CYD DEN-3
- (i) CYD DEN-3 and CYD DEN-4; (ii) CYD DEN-1 and VDV-2
- (i) VDV-1 and VDV-2; (ii) CYD DEN-3 and CYD DEN-4
- (i) VDV-1 and CYD DEN-3; (ii) VDV-2 and CYD DEN-4
- (i) VDV-1 and CYD DEN-4; (ii) VDV-2 and CYD DEN-3
- (i) VDV-2 and CYD DEN-3; (ii) VDV-1 and CYD DEN-4
- (i) VDV-2 and CYD DEN-4; (ii) VDV-1 and CYD DEN-3
- (i) CYD DEN-3 and CYD DEN-4; (ii) VDV-1 and VDV-2.

In the context of the present invention, the term "dose of vaccinal virus" is intended to mean a composition comprising an "immunoeffective amount" of the vaccinal virus, i.e. an amount of virus sufficient to induce a homologous neutralizing antibody response, which can be demonstrated, for example, by means of the seroneutralization test as described below in example 1. A serum is considered to be positive for the presence of neutralizing antibodies when the neutralizing antibody titer thus determined is greater than or equal to 1:10.

Vaccinal strain amounts are commonly expressed in terms of viral plaque-forming units (PFU) or of 50% tissue culture infectious dose ($TCID_{50}$), or else of 50% cell culture infectious dose ($CCID_{50}$). For example, the compositions according to the invention can contain from 10 to $10^6$ $CCID_{50}$, in particular from $10^3$ to $10^5$ $CCID_{50}$ of vaccinal dengue virus serotype 1, 2, 3 or 4 for a monovalent or bivalent composition. Thus, in the compositions or use according to the invention, the doses of vaccinal dengue viruses serotypes 1, 2, 3 and 4 are preferably each within a range of from 10 to $10^6$ $CCID_{50}$, such as 10, $10^1$, $10^2$, $10^3$, $10^4$, $10^5$ or $10^6$ $CCID_{50}$, in particular in a range from $10^3$ to $10^5$ $CCID_{50}$. The vaccinal viruses can be used at identical or different doses, which can be adjusted according to the nature of the vaccinal virus used and to the strength of the immune response obtained.

Preferably, the homologous neutralizing antibody response is long-lasting, i.e. it can be detected in the serum at least 6 months, after administration of the dengue serotypes (ii).

In the sequential administration according to the invention, the vaccinal dengue viruses of the third and fourth serotypes are administered at least 30 days and at most 12 months after the administration of the vaccinal dengue viruses of the first and second serotypes.

In the context of the present invention, the vaccinal dengue viruses of the third and fourth serotypes can, for example, be administered 30 days to 1 year, for example 30 days, 45 days, 60 days, 3 months, 6 months, 9 months or 1 year, advantageously 30 days to 3 months, in particular 1 to 2 months, after the administration of the vaccinal dengue viruses of the first and second serotypes.

The dose of a vaccinal dengue virus of a first serotype and the dose of a vaccinal dengue virus of a second serotype are administered simultaneously in the form of two monovalent compositions, or in the form of a single bivalent composition.

Similarly, the dose of a vaccinal dengue virus of a third serotype and the dose of a vaccinal dengue virus of a fourth serotype are administered simultaneously. For example, the third and fourth serotypes can be administered simultaneously in the form of two monovalent vaccinal compositions, or in the form of a single bivalent vaccinal composition.

The vaccinal viruses are administered in the form of vaccinal compositions which can be prepared according to any method known to those skilled in the art. Usually, the viruses, generally in lyophilized form, are mixed with a pharmaceutically acceptable excipient, such as water or a phosphate buffered saline solution, wetting agents or stabilizers. The term "pharmaceutically acceptable excipient" is intended to mean any solvent, dispersing medium, filler, etc., which does not produce a side reaction, for example an allergic reaction, in humans or animals. The excipient is selected according to the pharmaceutical form chosen, and to the method and route of administration. Appropriate excipients and also the requirements in terms of pharmaceutical formulation are described in "Remington: The Science & Practice of Pharmacy", which represents a reference work in the field.

Preferably, the vaccinal compositions are prepared in an injectable form, and can correspond to liquid solutions, suspensions or emulsions. The compositions can in particular include an aqueous solution buffered so as to maintain a pH of between approximately 6 and 9 (as determined with a pH meter at ambient temperature).

Although it is not necessary to add an adjuvant, the compositions can nevertheless include such a compound, i.e. a substance which increases, stimulates or strengthens the cellular or humoral immune response induced by the vaccinal strain administered simultaneously. Those skilled in the art are in a position to select, from the adjuvants conventionally used in the field of vaccines, an adjuvant which may be suitable in the context of the present invention.

The vaccinal compositions according to the invention can be administered according to any route normally used in immunization, for example parenterally (in particular intradermally, subcutaneously or intramuscularly). Preferably, the vaccinal compositions are injectable compositions administered subcutaneously in the deltoid region.

The volume of composition administered depends on the route of administration. For subcutaneous injections, the volume is generally between 0.1 and 1.0 ml, preferably approximately 0.5 ml.

The optimal period for the administration of the first and second serotypes, or preferably of all the serotypes 1 to 4, is approximately 1 to 3 months before exposure to the dengue virus. The vaccines can be administered as a prophylactic treatment for infection with a dengue virus in adults and children. Target populations therefore include individuals who may be naive (i.e. not previously immunized) or non-naive with respect to the dengue virus.

Vaccinal dengue virus serotypes 1 to 4 booster administrations can also be carried out, for example, between 6 months and 10 years, for example 6 months, 1 year, 3 years, 5 years or 10 years, after administration of the third and fourth serotypes.

The invention is illustrated by means of the following examples. All publications referred to herein are hereby incorporated by reference in their entirety.

EXAMPLES

Example 1

Sequential Immunization in Monkeys

The viremia and the immunogenicity were therefore tested in a monkey model. The viremia, in particular, was identified as one of the factors associated with the virulence and the severity of the disease in man and therefore constitutes an important parameter to be taken into consideration. The immunogenicity is, for its part, a key parameter in the context of the evaluation of the protection conferred.

1.1 Materials and Methods:

The experiments in monkeys were carried out according to the European Directives relating to animal experimentation. The immunizations were carried out in cynomolgus monkeys (*Macaca fascicularis*) originating from Mauritania. The monkeys were placed in quarantine for six weeks before immunization.

The monkeys were immunized subcutaneously in the arm(s) with 0.5 ml of vaccinal composition. After a light anesthesia with ketamine (Imalgene, Merial), blood was collected by puncture from the inguinal or saphenous veins. At day 0 and 28, 5 ml of blood were sampled in order to evaluate the antibody responses, while, between days 2 and 10, 1 ml of blood was sampled in order to evaluate the viremia. The blood was collected on ice and stored on ice until serum separation. To do this, the blood was centrifuged for 20 minutes at 4° C. and the serum collected was stored at −80° C. until the time of the tests.

Measurement of Viremia

The post-vaccinal viremias were monitored by quantitative real-time RP-PCR (qRT-PCR). Two sets of primers and of probes located in the NS5 gene of the DEN1 and DEN2 strains were used to quantify the VDV-1 RNA and VDV-2 RNA, respectively. A third set of primers and of probes located in the NS5 gene of the YF virus was used to quantify the CYD RNA. Finally, 4 sets of primers and of probes specific for the various serotypes, located at the junction of the E (DEN)/NS1 (YF) genes were used to identify the serotype in the samples positive for the YF NS5 RNA (see also table I). 7 plasmids containing, under the control of the T7 promoter, the region targeted by each PCR were transcribed in vitro so as to generate a series of synthetic RNAs which were included as an internal reference in each RT-PCR assay. These synthetic RNAs were assayed by spectrophotometry, and the amount of RNA obtained was converted to number of RNA copies and expressed as GEQ (genomic equivalents).

0.140 ml of monkey serum was extracted using the Macherey Nagel "Nucleospin 96 virus™" RNA extraction kit, according to the manufacturer's instructions, and then the purified RNA was eluted with 0.140 ml (0.090 ml, then 0.05 ml) of RNase-free water. In order to avoid repeated freezing/thawing cycles, a first quantification was carried out immediately after the extraction, on 5 μl of said RNA preparation. The remaining volume was frozen at 70° C.

The reaction mixtures contained, in addition to the components of the "Qiagen Qauntitect probes" RT-PCR quantification kit (Qiagen), 10 picomol of each primers, 4 picomol of each probe and 5 μl of RNA, in the total volume of 25 μl. In the case of the RNAs to be tested, 5 μl of the purified preparation were directly introduced into the reaction mixture, without any prior dilution step. The synthetic RNAs were diluted to 1/10 in RNAse-free water, and 7 dilutions containing approximately 10 to $10^6$ GEQ in 5 μl were quantified in parallel in order to generate the standard curve.

The quantification reactions were carried out on the Applied Biosystem ABIPrism 700™ device, using the following program: 50° C./30 min, 95° C./15 min, then 40 cycles of 95° C./15 sec-60° C./60 sec.

The limit of quantification of the viral RNA in this test is from 2.9 to 3.3 $\log_{10}$ GEQ/ml (800 to 2000 GEQ/ml; 4 to 10 GEQ/reaction), according to the PCR targets (standard deviation: ±0.3 $\log_{10}$).

The correlation between the infectious titer and the viral RNA quantification was established in parallel to the assays, by analysis of 0.140 ml of negative monkey serum samples (DO) to which a known amount of infectious particles of the viruses which were used for the immunization (CYD or VDV) were added. Said control sera were prepared at two dilutions containing approximately 1 PFU and approximately 100 PFU in 5 μl (2.3 and 4.3 $\log_{10}$ PFU/ml, respectively).

The primers and probes used are given in table 1 below, in which are listed, in order, for each assay, the sense and antisense primers and the probe.

TABLE 1

| | | sequence |
|---|---|---|
| YF | YF-NS5 sense | 5' GCACGGATGTAACAGACTGAAGA (23 bases) |
| | YF NS5 anti | 5' CCAGGCCGAACCTGTCAT (18 bases) |
| | YF-NS5 | 5' Fam- CGACTGTGTGGTCCGGCCCATC-Tamra (22 bases) |
| CYD1 | CYD1-sense | 5' CAT TGC AGT TGG CCT GGT AA (20 b) |
| spe | CYD1-anti | 5' CTT TGG CAA GAG AGA GCT CAA GT (23 b) |
| | CYD1- | 5' Fam-CCG ATC AAG GAT GCG CCA TCA-Tamra (21 b) |
| CYD2 | CYD2-sense | 5' GTG GGA GTC GTG ACG CTG TA (20 b) |
| spe | CYD2-anti | 5' GTT GAT GGC GCA TCC TTG ATC (21 b) |
| | CYD2 | 5' Fam-TGG GAG TTA TGG TGG GCG CCG-Tamra (21 b) |

TABLE 1-continued

| | | sequence |
|---|---|---|
| CYD3 spe | CYD3-sense CYD3-anti CYD3- | 5' AAA ACA CTT CCA TGT CAT TTT CAT G (25 b) 5' GTT GAT GGC GCA TCC TTG ATC (21 b) 5'Fam-TGCGATAGGAATTATCACACTCTATCTGGGAGC-Tamra (33 b) |
| CYD4 spe | GYD4-sense CYD4-anti CYD4- | 5' CTT AGT ATT GTG GAT TGG CAC GAA (24 b) 5' GCG CCA ACT GTG AAA CCT AGA (21 b) 5'-Fam-AGAAACACTTCAATGGCAATGACGTGCAT-Tamra (29 b) |
| VDV1 spe | VDV1-NS5 sense VDV1-NS5 anti VDV1-NS5 | 5' TCG CAA CAG CCT TAA CAG C (19 b) 5' ACT ATC CTC CCA TCC TTC (21 b) 5' Fam-TTC ACA CCA CTT CCA C-M GB/NFQ (16 b) |
| VDV2 spec | VDV2-NS5 sense VDV2-NS5 anti VDV2-NS5 | 5' AAT GAC AGA CAC GAC TCC (18 b) 5' CCC AAA ACC TAC TAT CTT CAA C (22 b) 5' Fam-TGG AAG TCG GCA CGT GA-MGB/NFQ (17 b) |

Measurement of Neutralizing Antibodies (Seroneutralization test)(SN50)

Conventionally, the dengue antibody measurement is established using the PRNT50 (50% PFU number reduction neutralization test). Since this test is laborious and uses up a lot of material, we developed the SN50 test, based on 50% reduction in the number of units measured in a CCID50 test.

In a 96-well plate, 0.120 ml of each decomplemented serum is added to 0.480 ml of diluent (ISCOVE 4% FCS) per well. 6-fold serial dilutions are prepared by transfer of 0.150 ml of serum into 0.450 ml of diluent. 450 µl of viural dilution at 2.7 $\log_{10}$ CCID50/ml are added to each well so as to obtain 25 CCID50/well. The plate is incubated at 37° C. for 1 hour. 100 µl of each dilution are then distributed into 6 wells of a 96-well plate into which VERO cells had been seeded 3 days before the beginning of the experiment at a density of 8000 cells/well, in 100 µl of ISCOVE medium containing 4% FCS. After incubation at 37° C. for 6 days, in the presence of 5% $CO_2$, the cells are fixed with an ethanol/acetone (70/30) mixture at 4° C. for 15 minutes, and then washed 3 times in PBS and incubated for 1 h at 37° C. in the presence of 50 µl of a 1/2000 dilution of an anti-flavivirus monoclonal antibody (mAb 4G2). The plates are then washed twice and incubated for 1 h at 37° C. in the presence of 50 µl of a 1/1000 dilution of an alkaline phosphatase-conjugated anti-mouse IgG. The lysis plaques are visualized by adding 50 µl of a colored substrate: BCIP/NBT. The neutralizing antibody titers are calculated using the Karber formula as defined below:

$$\log_{10} SN50 = d + f/N(X+N/2),$$

in which:
d represents the dilution resulting in 100% neutralization (i.e. 6 negative replicates, i.e. replicates exhibiting no sign of infection)
f: represents the dilution factor in log 10 (e.g. dilution factor of 1:4, f=0.6)
N: represents the number of replicates/dilution (N=6)
X: total number of wells exhibiting no sign of infection, with the exception of the dilution d.

The limit of viral detection is 10 SN50 (i.e. 1.0 $\log_{10}$SN50).

The viral strains which were used for the neutralization are the DEN1 16007, DEN2 16681, DEN3 16562 or DEN4 1036 strains.

For the controls, the initial viral dilutions were re-titrated.

The correlation between the neutralizing titer measured in the SN50 test and the neutralizing titer measured conventionally in the PRNT50 test is: $\log_{10}$ PRNT50=$\log_{10}$ SN50+0.2.

The mean titer (GMT) is established by calculating the geometric mean of the titers expressed as linear value; samples for which the titer is below the detection threshold are, by convention, given a value equal to half this threshold.

1.2 Evaluation of the Sequential Immunizations 3 groups of 4 monkeys of equivalent age and weight were immunized (see table 2).

The immunization was carried out subcutaneously in the arm, with a 23G1 needle, at a dose of $10^5$ $CCID_{50}$ for each serotype for the CYD DEN 1 to 4 vaccines. VDV-1 and VDV-2 were injected at a dose of 3.96 $\log_{10}$ and 4.84 $\log_{10}$, respectively.

TABLE 2

Composition of the groups and immunization protocol

| | No of the | Immunizations | |
|---|---|---|---|
| Group | monkeys | D0 | D56 |
| 1 | AM633 AM634 AM941 AN045 | VDV-1,2 (bivalent composition) | CYD-3,4 (bivalent composition) |
| 2 | AM637 AN002 AN013 AN073 | CYD-1,2 (bivalent composition) | CYD-3,4 (bivalent composition) |
| 3 | AM496 AM645 AM766 AM813 | CYD-1,2,3,4 (tetravalent composition) | CYD-1,2,3,4 (tetravalent composition) |

The immunogenicity results obtained after one immunization (D28) and two immunizations (D84) are given in table 3.

The viremia results are given in table 4.

TABLE 3

| | Monkeys | | | SN50 neutralizing titer | | | | | | |
| | | Immunizations | | D + 28 | | | | D + 84 | | | |
| Group | ID | D0 | D56 | DEN-1 | DEN-2 | DEN-3 | DEN-4 | DEN-1 | DEN-2 | DEN-3 | DEN-4 |
|---|---|---|---|---|---|---|---|---|---|---|---|
| 1 | AM633 | VDV 12 | CYD 34 | 16 | 10 | — | — | 20 | 126 | 20 | 126 |
| | AM634 | | | 126 | 200 | — | — | 319 | 802 | 100 | 637 |
| | AM941 | | | 32 | 200 | — | — | 252 | 802 | 40 | 252 |
| | AN045 | | | 25 | 200 | — | — | 63 | 400 | 50 | 252 |
| | geometric mean | | | 35 | 94 | — | — | 100 | 425 | 45 | 268 |
| 2 | AM637 | CYD 12 | CYD 34 | 32 | 10 | — | — | 637 | 31 | 40 | 159 |
| | AN002 | | | 40 | 31 | — | — | 1277 | 634 | 100 | 159 |
| | AN013 | | | 20 | 316 | — | — | 20 | 400 | 20 | 16 |
| | AN073 | | | — | — | — | — | 63 | 126 | 40 | 504 |
| | geometric mean | | | 19 | 27 | — | — | 179 | 178 | 42 | 119 |
| 3 | AM496 | CYD 1234 | CYD 1234 | 50 | — | 16 | 32 | 100 | 40 | 80 | 252 |
| | AM645 | | | — | — | 13 | 31 | 16 | — | — | 63 |
| | AM766 | | | — | — | — | 32 | 20 | — | — | 80 |
| | AM813 | | | 25 | — | — | 13 | 63 | 13 | 20 | 63 |
| | geometric mean | | | 13 | — | 8 | 25 | 38 | 11 | 14 | 95 |

— = <−10 $SN_{50}$ corresponding to the limit of sensitivity of the test (titer = 5 for the calculation of the geometric mean)*

TABLE 4

Viremia titers
Monitoring of post vaccinal viremias of the F IM DEN011 Mk monkey study

| | | | 1st immunization (D0) | | | | | | | | |
| Group | Monkey | type | D2 | D3 | D4 | D5 | D6 | D7 | D8 | D9 | D10 |
|---|---|---|---|---|---|---|---|---|---|---|---|
| 1 | AM633 | VDV1 | — | — | — | — | — | — | — | — | — |
| | | VDV2 | — | — | — | — | 3.928 | — | 3.54 | — | — |
| (i)VDV 1.2 | AM634 | VDV1 | — | — | — | — | — | — | — | — | — |
| (ii)CYD3.4 | | VDV2 | — | 4.08 | 4.75 | 5.14 | 5.38 | 2.93 | 4.42 | 3.42 | — |
| | AM941 | VDV1 | — | — | — | — | — | — | — | — | — |
| | | VDV2 | 4.191 | — | 4.015 | 4.341 | 4.897 | 4.894 | 4.276 | — | 2.754 |
| | AN045 | VDV1 | — | — | — | — | — | — | — | — | — |
| | | VDV2 | 3.446 | — | 4.108 | 4.905 | 4.968 | 4.749 | 3.175 | 2.908 | — |
| 2 | AM637 | CYD1 | 3.32 | — | — | — | — | — | — | — | — |
| | | CYD2 | — | — | — | — | — | — | — | — | — |
| (i)CYD1.2 | AN002 | CYD1 | — | — | — | — | — | — | — | — | — |
| (ii)CYD3.4 | | CYD2 | — | — | — | — | — | — | — | — | — |
| | AN013 | CYD1 | — | — | — | — | — | — | — | — | — |
| | | CYD2 | — | — | — | — | — | — | — | — | — |
| | AN073 | CYD1 | — | — | — | — | — | — | — | — | — |
| | | CYD2 | — | — | — | — | — | — | — | — | — |
| 6 | AM496 | CYD1 | — | — | — | — | — | — | — | — | — |
| | | CYD2 | — | — | — | — | — | — | — | — | — |
| (i)CYD1-4 | | CYD3 | — | — | — | — | — | — | — | — | — |
| (ii)CYD1-4 | | CYD4 | 4.221 | 3.363 | 3.711 | 4.154 | 3.145 | — | 3.579 | — | — |
| | AM645 | CYD1 | 3.27 | — | — | — | — | — | — | — | — |
| | | CYD2 | — | — | — | — | — | — | — | — | — |
| | | CYD3 | 3.55 | — | — | — | — | — | — | — | — |
| | | CYD4 | 3.66 | 3.607 | 2.82 | 3.514 | 3.654 | 3.238 | — | 3.475 | 3.443 |
| | AM766 | CYD1 | — | — | — | — | — | — | — | — | — |
| | | CYD2 | — | — | — | — | — | — | — | — | — |
| | | CYD3 | — | — | — | — | — | — | — | — | — |
| | | CYD4 | 3.966 | 3.06 | 3.378 | 4.193 | 3.80 | 3.729 | — | — | — |
| | AM813 | CYD1 | — | — | — | — | — | — | — | — | — |
| | | CYD2 | — | — | — | — | — | — | — | — | — |
| | | CYD3 | — | — | — | — | — | — | — | — | — |
| | | CYD4 | 4.813 | 4.603 | 3.173 | 2.85 | — | — | — | — | — |

TABLE 4-continued

Viremia titers
Monitoring of post vaccinal viremias of the F IM DEN011 Mk monkey study

| Group | Monkey | type | 2nd immunizaton (D56) | | | | | | | | |
|---|---|---|---|---|---|---|---|---|---|---|---|
| | | | D58 | D59 | D60 | D61 | D62 | D63 | D64 | D65 | D66 |
| 1 | AM633 | CYD3 | — | — | — | — | — | — | — | — | — |
| | | CYD4 | 3.613 | — | — | — | — | 3.075 | — | — | — |
| (i)VDV 1.2 | AM634 | CYD3 | — | — | — | — | — | — | — | — | — |
| (ii)CYD3.4 | | CYD4 | — | — | — | — | — | 2.986 | — | — | — |
| | AM941 | CYD3 | — | — | — | — | — | — | — | — | — |
| | | CYD4 | — | — | — | — | — | 3.444 | — | — | — |
| | AN045 | CYD3 | — | — | — | — | — | — | — | — | — |
| | | CYD4 | 2.97 | — | — | 2.95 | — | 3.344 | 3.509 | 3.40 | — |
| 2 | AM637 | CYD3 | — | — | — | — | — | — | — | — | — |
| | | CYD4 | 5.209 | 4.629 | 3.664 | 2.985 | — | — | — | — | — |
| (i)CYD1.2 | AN002 | CYD3 | — | — | — | — | — | — | — | — | — |
| (ii)CYD3.4 | | CYD4 | 3.559 | — | — | — | 3.674 | 3.835 | 3.573 | 3.587 | 3.30 |
| | AN013 | CYD3 | — | — | — | — | — | — | — | — | — |
| | | CYD4 | — | — | — | — | — | — | — | — | — |
| | AN073 | CYD3 | — | — | — | — | — | — | — | — | — |
| | | CYD4 | 3.73 | 3.50 | 3.111 | 2.8 | 3.337 | — | 3.068 | 3.284 | — |
| 6 | AM496 | CYD1 | — | — | — | — | — | — | — | — | — |
| | | CYD2 | — | — | — | — | — | — | — | — | — |
| (i)CYD1-4 | | CYD3 | — | — | — | — | — | — | — | — | — |
| (ii)CYD1-4 | | CYD4 | — | — | — | — | — | — | — | — | — |
| | AM645 | CYD1 | — | — | — | — | — | — | — | — | — |
| | | CYD2 | — | — | — | — | — | — | — | — | — |
| | | CYD3 | — | — | — | — | — | — | — | — | — |
| | | CYD4 | — | — | — | — | — | — | — | — | — |
| | AM766 | CYD1 | — | — | — | — | — | — | — | — | — |
| | | CYD2 | — | — | — | — | — | — | — | — | — |
| | | CYD3 | — | — | — | — | — | — | — | — | — |
| | | CYD4 | — | — | — | — | — | — | — | — | — |
| | AM813 | CYD1 | — | — | — | — | — | — | — | — | — |
| | | CYD2 | — | — | — | — | — | — | — | — | — |
| | | CYD3 | — | — | — | — | — | — | — | — | — |
| | | CYD4 | — | — | — | — | — | — | — | — | — |

Correlation Between GEQ and PFU

GEQ/PFU ratio of 2.7 $\log_{10}$ (i.e.: 1 PFU=500 GEQ) for the sera positive with respect to YF or CYDs GEQ/PFU ratio of 2.5 $\log_{10}$ (i.e.: 1 PFU=320 GEQ) for the sera positive with respect to VDV1 or VDV2

Quantification limits:

<3.3 $\log_{10}$ GEQ/ml (i.e.: <4 PFU/ml) for the qRT-PCRs with respect to YF and CYDs <2.9 $\log_{10}$ GEQ/ml (i.e.: <2.5 PFU/ml) for the qRT-PCRs with respect to VDV1 and VDV2

Briefly, the results can be summarized as follows:

The administration scheme according to the present invention makes it possible to qualitatively and quantitatively increase the homologous neutralizing antibody response which is obtained with the tetravalent immunization.

The bivalent immunization CYD-1,2 followed two months later by an immunization CYD-3,4 induces high homologous responses against the four serotypes in all the monkeys. Similarly, the same good responses are observed after an administration of VDV-1,2 followed by CYD-3,4.

A notable result is the strong stimulatory effect of the CYD-3,4 serotypes on the responses induced by CYD-1,2 after primary immunization. An increase in the homologous, but also heterologous, neutralizing antibody responses can be noted. This phenomenon could be explained by a positive helper effect of the anti-NS-yellow fever response on the anti-E responses, without immunodominance. E epitopes with cross reactivity may also play a role. Paradoxically, this stimulating effect is not observed after a tetravalent booster, insofar as only the dominant E responses induced after primary immunization (here, 3) are boosted.

The viremia (table 4) is predominantly caused by CYD-4 in the case of the CYD vaccines and no difference is observed between two sequential bivalent administrations and one tetravalent administration (group 2 versus group 3). Thus, no difference in terms of safety after two bivalent immunizations or one tetravalent immunization is expected. A tendency toward a lower viremia is even rather observed with the vaccinal scheme according to the invention; see, for example, group 2 compared with group 3.

Example 2

Sequential Immunization in Monkeys Carried Out with a 1 Month Interval. Comparison of Schemes CYD-1,2 Followed by CYD-3,4 Versus CYD-2,3 Followed by CYD-1,4

The viremia and the immunogenicity were tested in a monkey model as in the previous example. In the present example, a one-month interval was used between the two immunizations, against two months in the previous example. The primary immunization carried out with the two vaccinal viruses that are the least immunogenic in monkeys (CYD-2,3) is followed by an administration with the two immunodominant vaccinal viruses (CYD-1,4).

2.1 Materials and Methods: Identical to Example 1

2.2 Evaluation of Sequential Immunizations with a One-Month Interval 3 groups of 4 monkeys of equivalent age and weight were immunized. (see table 5).

The immunization was carried out subcutaneously in the arm with a 23G1 needle, at a dose of $10^5$ $CCID_{50}$ for each serotype for the vaccinal viruses CYD DEN 1 to 4 as previously.

TABLE 5

Group composition and immunization protocol

| Group | Immunizations | |
| --- | --- | --- |
| | D0 | D28 |
| 1 | CYD Tetrav (5555) | CYD Tetrav (5555) |
| 2 | CYD Biv 1-2 (55) | CYD Biv 3-4 (55) |
| 3 | CYD Biv 2-3 (55) | CYD Biv 1-4 (55) |

The immunogenicity results obtained after one immunization (D28) and two immunizations (D56) are given in table 6.

The viremia results are similar to those given in example 1, showing a weak viremia induced by CYD4 and no significant difference between the various groups.

Briefly, the results complete those obtained in example 1 and can be summarized as follows:

The administration scheme according to the present invention makes it possible to qualitatively and quantitatively increase the homologous neutralizing antibody response that is obtained with the tetravalent vaccination when the two immunizations are carried out with a 1 month interval.

The CYD-1,2 bivalent immunization followed, one month later, by a CYD-3,4 immunization (group 2) induces high homologous responses against the four serotypes in all the monkeys, with serotypes 1 and 4 being dominant.

In this group, the booster effect on serotypes 1 and 2 is less marked when the second administration is carried out after one month, than when it is carried out after 2 months as in example 1.

When the immunizations begin with the less immunogenic serotypes (CYD-2,3) and the booster is carried out with the strongest serotypes (CYD-1,4), the response obtained is better balanced, with less dominance of serotypes 1 and 4 (group 3).

These results confirm those obtained in example 1, which show that an immunization carried out sequentially with two bivalents is effective in inducing a response against all the serotypes in all the animals, even when the booster is carried out only 1 month after the primary immunization.

TABLE 6

| | | Monkeys Immunizations | | SN50 D0 + 24 | | | | D0 + 56 | | | |
| --- | --- | --- | --- | --- | --- | --- | --- | --- | --- | --- | --- |
| Group | ID | D0 | D28 | DEN-1 | DEN-2 | DEN-3 | DEN-4 | DEN-1 | DEN-2 | DEN-3 | DEN-4 |
| 1 | AR193 | CYD | CYD | 160 | 80 | 32 | 638 | 638 | 63 | 40 | 401 |
| | AR197 | Tetrav | Tetrav | 50 | — | — | 318 | 32 | 16 | 10 | 401 |
| | AR209 | (5555) | (5555) | 100 | — | — | 159 | 160 | 16 | 32 | 317 |
| | AR335 | | | 40 | — | — | 505 | 126 | 25 | — | 100 |
| | Geometric mean | | | 75 | — | — | 357 | 142 | 25 | 23 | 267 |
| 2 | AR162 | CYD Biv | CYD Biv | 1604 | 63 | ND | ND | 1274 | 50 | 63 | 318 |
| | AR230 | 1-2 | 3-4 | 32 | — | ND | ND | 100 | 63 | 12 | 160 |
| | AR264 | (55) | (55) | 1274 | 63 | ND | ND | 635 | 25 | 40 | 401 |
| | AR336 | | | 4048 | — | ND | ND | 2019 | 13 | 126 | 401 |
| | Geometric mean | | | 715 | 21 | ND | ND | 636 | 32 | 44 | 301 |
| 3 | AR156 | CYD Biv | CYD Biv | ND | — | 318 | ND | 32 | 25 | 126 | 126 |
| | AR173 | 2-3 | 1-4 | ND | 25 | 80 | ND | 63 | 50 | 80 | 253 |
| | AR337 | (55) | (55) | ND | 32 | — | ND | 40 | 63 | 160 | 401 |
| | AR367 | | | ND | 50 | 100 | ND | 32 | 80 | 126 | 126 |
| | Geometric mean | | | ND | 18 | 50 | ND | 40 | 50 | 119 | 200 |

ND: not determined

— = <10 $SN_{50}$ corresponding to the limit of sensitivity of the test

What is claimed is:

1. A method of inhibiting disease caused by a dengue virus infection, the method comprising:
   a) in a first administration, administering to a subject an effective amount of a first and second vaccinal dengue virus serotype; and
   b) in a second administration, administering to the subject an effective amount of a third and fourth vaccinal dengue virus serotype
   wherein
   i) the first, second, third, and fourth vaccinal dengue virus serotypes are each different one from another;
   ii) the second administration occurs from about 30 days to about 1 year after the first administration;
   iii) each vaccinal dengue virus serotypes is administered in an amount that is sufficient to induce a homologous immune response;
   iv) the first and second serotypes are administered in separate dosages forms or together in a single dosage form;
   v) the third and fourth serotypes are administered in separate dosages forms or together in a single dosage form; and
   vi) each of the dengue virus serotypes is a live, attenuated virus.

2. The method according to claim 1 wherein the third and fourth serotypes are administered in a single dosage form.

3. The method according to claim 1 wherein the first and second serotypes are administered in a single dosage form.

4. The method according to claim 1 wherein the first or second vaccinal dengue virus serotype is selected from the group consisting of the VDV1 strain and of a CYD DEN-1.

5. The method according to claim 1 wherein the first or second vaccinal dengue virus serotype is selected from the group consisting of the VDV2 strain and of a CYD DEN-2.

6. The method according to claim 1 wherein the first vaccinal dengue virus serotype is the VDV1 strain and the second vaccinal dengue virus serotype is the VDV2 strain.

7. The method according to claim 1 wherein the first vaccinal dengue virus serotype is a CYD DEN-1 and the second vaccinal dengue virus serotype 2 is a CYD DEN-2.

8. The method according to claim 1 wherein the third vaccinal dengue virus serotype is a CYD DEN-3.

9. The method according to claim 1 wherein the fourth vaccinal dengue virus serotype 4 is a CYD DEN-4.

10. The method according to claim 1 wherein first and second serotypes are CYD DEN1 and CYD DEN2 and the third and fourth serotypes are CYD DEN3 and CYD DEN4.

11. The method according to claim 1 wherein the third and fourth serotypes are administered 30 days to 3 months after the administration of the first and second serotypes.

12. The method according to claim 1 wherein the third and fourth serotypes are administered 30 days after the administration of the first and second serotypes.

13. The method according to claim 1 wherein the dosage forms comprise the vaccinal dengue viruses serotypes in a range of from $10^3$ to $10^5$ $CCID_{50}$.

* * * * *

SEQUENCE LISTING

<160> NUMBER OF SEQ ID NOS: 2

<210> SEQ ID NO 1
<211> LENGTH: 10735
<212> TYPE: DNA
<213> ORGANISM: Dengue virus

<400> SEQUENCE: 1
agttgttagt ctacgtggac cgacaagaac agtttcgaat cggaagcttg cttaacgtag 60
ttctaacagt tttttattag agagcagatc tctgatgatc aaccaacgaa aaaagacggg 120
tcgaccgtct ttcaatatgc tgaaacgcgc gagaaaccgc gtgtcaactg tttcacagtt 180
ggcgaagaga ttctcaaaag gattgctctc aggccaagga cccatgaaat tggtgatggc 240
tttcatagca ttcttaagat ttctagccat acccccaaca gcaggaattt tggctagatg 300
gggctcattc aagaagaatg gagcgattaa agtgttacgg ggtttcaaga gagaaatctc 360
aaacatgcta aacataatga acaggaggaa aagatccgtg accatgctcc ttatgctgct 420
gcccacagcc ctggcgttcc atctgacgac acgaggggga gagccgcata tgatagttag 480
caagcaggaa agaggaaagt cacttttgtt caagacctct gcaggtgtca acatgtgcac 540
cctcattgcg atggatttgg gagagttgtg tgaggacacg atgacctaca aatgccccg 600 gatcactgag gcggaaccag atgacgttga ctgttggtgc aatgccacgg acacatgggt 660
gacctatgga acgtgctctc aaactggcga acaccgacga gacaaacgtt ccgtcgcatt 720
ggccccacac gtggggcttg gcctagaaac aagagccgaa acgtggatgt cctctgaagg 780
tgcttggaaa cagatacaaa aagtagagac ttgggctctg agacatccag gattcacggt 840
gatagccctt tttctagcac atgccatagg aacatccatc acccagaaag ggatcatttt 900
cattttgctg atgctggtaa caccatctat ggccatgcga tgcgtgggaa taggcaacag 960
agacttcgtg gaaggactgt caggagcaac atgggtggat gtggtactgg agcatggaag 1020
ttgcgtcacc accatggcaa aaaacaaacc aacactggac attgaactct tgaagacgga 1080
ggtcacaaac cctgcagttc tgcgtaaatt gtgcattgaa gctaaaatat caaacaccac 1140
caccgattcg agatgtccaa cacaaggaga agccacactg gtggaagaac aagacgcgaa 1200
ctttgtgtgc cgacgaacgt tcgtggacag aggctggggc aatggctgtg ggctattcgg 1260
aaaaggtagt ctaataacgt gtgccaagtt taagtgtgtg acaaaactag aaggaaagat 1320
agctcaatat gaaaacctaa aatattcagt gatagtcacc gtccacactg gagatcagca 1380
ccaggtggga aatgagacta cagaacatgg aacaactgca accataacac ctcaagctcc 1440
tacgtcggaa atacagctga ccgactacgg aacccttaca ttagattgtt cacctaggac 1500
agggctagat tttaacgaga tggtgttgct gacaatgaaa aagaaatcat ggcttgtcca 1560
caaacagtgg tttctagact taccactgcc ttggacctct ggggctttaa catcccaaga 1620
gacttggaac agacaagatt tactggtcac atttaagaca gctcatgcaa agaagcagga 1680
agtagtcgta ctaggatcac aagaaggagc aatgcacact gcgctgactg gagcgacaga 1740
aatccaaacg tcaggaacga caacaatttt cgcaggacac ctaaaatgca gactaaaaat 1800
ggacaaacta actttaaaag ggatgtcata tgtgatgtgc acaggctcat tcaagttaga 1860
gaaagaagtg gctgagaccc agcatggaac tgttctggtg caggttaaat atgaaggaac 1920
agacgcacca tgcaagattc ccttttcgac ccaagatgag aaaggagcaa cccagaatgg 1980
gagattaata acagccaacc ccatagtcac tgacaaagaa aaaccagtca atattgaggc 2040

```
agaaccaccc tttggtgaga gctacatcgt ggtaggagca ggtgaaaaag ctttgaaact   2100
aagctggttc aagaaaggaa gcagcatagg gaaaatgttt gaagcaactg cccgaggagc   2160
acgaaggatg gccattctgg gagacaccgc atgggacttc ggttctatag gaggagtgtt   2220
cacgtctatg ggaaaactgg tacaccaggt ttttggaact gcatatggag ttttgtttag   2280
cggagtttct tggaccatga aaataggaat agggattctg ctgacatggc taggattaaa   2340
ttcaaggaac acgtcccttt cggtgatgtg catcgcagtt ggcatggtca cactgtacct   2400
aggagtcatg gttcaggcag attcgggatg tgtaatcaac tggaaaggca gagaacttaa   2460
atgtggaagc ggcatttttg tcactaatga agttcacact tggacagagc aatacaaatt   2520
ccaggctgac tcccccaaga gactatcagc agccattggg aaggcatggg aggagggtgt   2580
gtgtggaatc cgatcagcca ctcgtctcga gaacatcatg tggaaacaaa tatcaaatga   2640
attgaaccac atcctacttg aaaatgacat gaaatttaca gtggtcgtgg agacgttag    2700 tggaatcttg gcccaaggaa aaaaatgat taggccacaa cccatggaac acaaatactc    2760
gtggaaaagc tggggaaaag ctaaaatcat aggagcggat gtacagaaca ccaccttcat   2820
catcgacggc ccaaacaccc cagaatgccc tgacaatcaa agagcatgga atatttggga   2880
agtagaggac tatggatttg gattttcac gacaaacata tggttgaaat tgcgtgactc   2940
ctacacccaa gtatgtgacc accggctgat gtcagctgcc attaaggaca gcaaggcagt   3000
ccatgctgac atggggtact ggatagaaag tgaaaagaac gagacatgga gttggcgag    3060 agcctccttt atagaagtta agacatgcat ctggccaaaa tcccacactc tatggagcaa   3120
tggagttctg gaaagtgaaa tgataattcc aaagatatat ggaggaccaa tatctcagca   3180
caactacaga ccaggatatt tcacacaaac agcagggccg tggcacctag caagttgga    3240 actagatttc gattttgtg aaggtaccac agttgttgtg atgaacatt gtggaaatcg      3300 aggaccatct ctcagaacca caacagtcac aggaaagata atccatgaat ggtgctgcag   3360
atcttgtacg ctacccccc tacgtttcaa aggggaagac gggtgttggt acggcatgga    3420
aatcagacca gtgaaggaca aggaagagaa cctggtcaag tcaatggtct ctgcagggtc   3480
aggagaagtg gacagctttt cactaggact gctatgcata tcaataatga ttgaagaagt   3540
gatgagatcc agatggagca aaaaaatgct gatgactgga acactggctg tgttcctcct   3600
tcttataatg ggacaattga catggagtga tctgatcagg ttatgtatta tggttggagc   3660
caacgcttca gacaagatgg ggatgggaac aacgtaccta gctttaatgg ccactttcaa   3720
aatgagacca atgttcgccg tcgggctatt atttcgcaga ctaacatcta gagaagttct   3780
tcttcttaca attggcttga gcctggtggc atccgtggag ctaccaagtt ccctagagga   3840
gctgggggat ggacttgcaa taggcatcat gatgttgaaa ttattgactg attttcagtc   3900
acaccagcta tgggctactc tgctatcctt gacatttatt aaaacaactt tttcattgca   3960
ctatgcatgg aagacaatgg ctatggtact gtcaattgta tctctcttcc ctttatgcct   4020
gtccacgacc tctcaaaaaa caacatggct tccggtgctg ttgggatctc ttggatgcaa   4080
accactaccc atgtttctta acagaaaaa caaaatctgg ggaaggaaga gttggcccct   4140
caatgaagga attatggctg ttggaatagt tagtattcta ctaagttcac ttttaaaaaa   4200
tgatgtgccg ctagccggcc cattaatagc tggaggcatg ctaatagcat gttatgtcat   4260
atccggaagc tcagctgatt tatcactgga gaaagcggct gaggtctcct gggaggaaga   4320
agcagaacac tcaggcgcct cacacaacat actagtagag gttcaagatg atggaaccat   4380
```

```
gaagataaaa gatgaagaga gagatgacac gctcaccatt ctccttaaag caactctgct   4440
ggcagtctca ggggtgtacc caatgtcaat accagcgacc cttttttgtgt ggtattttg   4500 gcagaaaaag aaacagagat caggagtgct atgggacaca cccagccccc cagaagtgga   4560
aagagcagtt cttgatgatg gcatctatag aattttgcaa agaggactgt tgggcaggtc   4620
ccaagtagga gtaggagttt tccaagaagg cgtgttccac acaatgtggc acgtcactag   4680
gggagctgtc ctcatgtatc aaggaaaaag gctggaacca agctgggcca gtgtcaaaaa   4740
agacttgatc tcatatggag gaggttggag gtttcaagga tcctggaaca cgggagaaga   4800
agtacaggtg attgctgttg aaccgggaaa aaaccccaaa aatgtacaaa caacgccggg   4860
taccttcaag acccctgaag gcgaagttgg agccatagcc ttagacttta aacctggcac   4920
atctggatct cccatcgtaa acagagaggg aaaaatagta ggtctttatg gaaatggagt   4980
ggtgacaaca agcggaactt acgttagtgc catagctcaa gctaaggcat cacaagaagg   5040
gcctctacca gagattgagg acaaggtgtt taggaaaaga aacttaacaa taatggacct   5100
acatccagga tcgggaaaaa caagaagata ccttccagcc atagtccgtg aggccataaa   5160
aaggaagctg cgcacgctaa tcctagctcc cacaagagtt gtcgcttctg aaatggcaga   5220
ggcactcaag ggagtgccaa taaggtatca gacaacagca gtgaagagtg aacacacagg   5280
aaaggagata gttgacctta tgtgccacgc cactttcacc atgcgcctcc tgtctcccgt   5340
gagagttccc aattataaca tgattatcat ggatgaagca cacttcaccg atccagccag   5400
catagcagcc agagggtaca tctcaacccg agtgggtatg ggtgaagcag ctgcgatctt   5460
tatgacagcc actcccccag gatcggtgga ggccttttcca cagagcaatg caattatcca   5520
agatgaggaa agagacattc ctgagagatc atggaactca ggctatgact ggatcactga   5580
ttttccaggt aaaacagtct ggtttgttcc aagcatcaaa tcaggaaatg acattgccaa   5640
ctgtttaaga aaaaacggga aacggtgat ccaattgagc agaaaaacct ttgacactga   5700
gtaccagaaa acaaaaaaca acgactggga ctatgtcgtc acaacagaca tttccgaaat   5760
gggagcaaat ttccgggccg acagggtaat agacccaagg cggtgtctga accggtaat   5820 actaaaagat ggtccagagc gcgtcattct agccggaccg atgccagtga ctgtggccag   5880
tgccgcccag aggagaggaa gaattggaag gaaccaaaac aaggaaggtg atcagtatat   5940
ttacatggga cagcctttaa aaaatgatga ggaccacgct cattggacag aagcaaagat   6000
gctccttgac aatataaaca caccagaagg gattatccca gccctctttg agccggagag   6060
agaaaagagt gcagctatag acgggaata cagactgcgg ggtgaagcaa ggaaaacgtt   6120
cgtggagctc atgagaagag gggatctacc agtctggcta tcctacaaag ttgcctcaga   6180
aggcttccag tactccgaca gaaggtggtg cttcgatggg gaaaggaaca ccaggtgtt   6240 ggaggagaac atggacgtgg agatctggaa aaagaagga gaaagaaga aactacgacc   6300 tcgctggttg gacgccagaa catactctga cccactggct ctgcgcgagt ttaaagagtt   6360
tgcagcagga agaagaagcg tctcaggtga cctaatatta gaaatagga aacttccaca   6420 acatttgacg caagggcccc agaatgcttt ggacaacttg gtcatgttgc acaattccga   6480
acaaggagga aaagcctata gacatgctat ggaagaactg ccagacacaa tagaaacgtt   6540
gatgctccta gccttgatag ctgtgttgac tggtggagtg acgctgttct tcctatcagg   6600
aagaggtcta ggaaaaacat ctatcggctt actctgcgtg atggcctcaa gcgcactgtt   6660
atggatggcc agtgtggagc cccattggat agcggcctcc atcatactgg agttcttct   6720 gatggtactg cttattccag agccagacag acagcgcact ccacaggaca accagctagc   6780
```

```
atatgtggtg ataggtctgt tattcgtgat attgacagtg gcagccaatg agatgggatt    6840
attggaaacc acaaagaaag acctggggat tggccatgta gctgctgaaa accaccacca    6900
tgctacaatg ctggacgtag acctacatcc agcttcagcc tggaccctct atgcagtggc    6960
cacaacaatc atcactccta tgatgagaca cacaattgaa aacacaacgg caaatatttc    7020
cctgacagcc atcgcaaacc aagcagctat attgatggga cttgacaagg gatggccaat    7080
atcgaagatg gacataggag ttccacttct cgccttgggg tgctattccc aagtgaatcc    7140
gctgacactg atagcggcag tattgatgct agtagctcat tacgccataa ttggacctgg    7200
actgcaagca aaagctacta gagaagctca aaaaagaaca gcggctggaa taatgaaaaa    7260
tccaactgtc gacgggattg ttgcaataga cttagatccc gtggtttacg atgcaaaatt    7320
tgaaaaacag ctaggccaaa taatgttgtt gatactttgc acatcacaga ttcttttgat    7380
gcggactaca tgggccttgt gtgaatccat cacattggct actggacctc tgaccactct    7440
ttgggaggga tctccaggaa aattctggaa caccacaata gcggtatcca tggcaaacat    7500
tttcaggggg agttatctag caggagcagg tctggccttc tcattaatga aatctctagg    7560
aggaggtagg agaggcacgg gagcccaagg ggaaacactg ggagaaaaat ggaaaagaca    7620
actaaaccaa ctgagcaagt cagaattcaa tacttacaag aggagtggga ttatggaggt    7680
ggatagatcc gaagccaaag agggactgaa aagaggagaa acaaccaaac acgcagtatc    7740
gagaggaacg gccaaactga ggtggttcgt ggagaggaac cttgtgaaac cagaagggaa    7800
agtcatagac ctcggttgtg gaagaggtgg ctggtcatat tattgcgctg ggctgaagaa    7860
agtcacagaa gtgaaaggat acacaaaagg aggacctgga catgaggaac caatcccaat    7920
ggcgacctat ggatggaacc tagtaaggct gcactccgga aaagatgtat tttttatacc    7980
acctgagaaa tgtgacaccc ttttgtgtga tattggtgag tcctctccga acccaactat    8040
agaggaagga agaacgttac gtgttctgaa aatggtggaa ccatggctca gaggaaacca    8100
attttgcata aaaattctaa atccctatat gccgagcgtg gtagaaactc tggaacaaat    8160
gcaaagaaaa catggaggaa tgctagtgcg aaacccactc tcaagaaatt ccacccatga    8220
aatgtactgg gtttcatgtg gaacaggaaa cattgtgtca gcagtaaaca tgacatctag    8280
aatgttgcta aatcggttca atgggctca caggaagcca acatatgaaa gagacgtgga    8340
cttaggcgct ggaacaagac atgtggcagt agaaccagag gtagccaacc tagatatcat    8400
tggccagagg atagagaata taaaaaatga acataagtca acatggcatt atgatgagga    8460
caatccatac aaaacatggg cctatcatgg atcatatgag gttaagccat caggatcggc    8520
ctcatccatg gtcaatggcg tggtgagatt gctcaccaaa ccatgggatg ttatccccat    8580
ggtcacacaa atagccatga ctgataccac acccttgga caacagaggg tgtttaaaga    8640
gaaagttgac acgcgcacac caaaagcaaa acgtggcaca gcacaaatta tggaagtgac    8700
agccaggtgg ttatggggtt tcctttctag aaacaaaaaa cccagaattt gcacaagaga    8760
ggagtttaca agaaaagtta ggtcaaacgc agctattgga gcagtgttcg ttgatgaaaa    8820
tcaatggaac tcggcaaaag aagcagtgga agacgaacgg ttctgggaac ttgtccacag    8880
agagagggag cttcataaac aggggaaatg tgccacgtgt gtctacaata tgatggggaa    8940
gagagagaaa aaattaggag agttcggaaa ggcaaaagga agtcgtgcaa tatggtacat    9000
gtggttggga gcacgcttcc tagagtttga agcccttggt ttcatgaatg aagatcactg    9060
gttcagtaga gagaattcac tcagtggagt ggaaggagaa ggactccaca aacttggata    9120
```

-continued

| | |
|---|---|
| catactcaga gacatatcaa ggattccagg ggggaacatg tatgcagatg acacagccgg | 9180 |
| atgggacaca agaataacag aggatgatct ccagaatgag gctaaaatca ctgacatcat | 9240 |
| ggagcccgaa catgccctgc tggctacgtc aatctttaag ctgacctacc aaaataaggt | 9300 |
| ggtaagggtg cagagaccag caaaaaatgg aaccgtgatg gatgttatat ccagacgtga | 9360 |
| ccagagaggc agtggacagg ttggaactta tggcttaaac actttcacca acatggaggc | 9420 |
| ccaactgata agacaaatgg agtctgaggg aatcttttta cccagcgaat ggaaaccccc | 9480 |
| aaatctagcc ggaagagttc tcgactggtt ggaaaaatat ggtgtcgaaa ggctgaaaag | 9540 |
| aatggcaatc agcggagatg actgtgtggt gaaaccaatt gatgacaggt tcgcaacagc | 9600 |
| cttaacagct ttgaatgaca tgggaaaagt aagaaaagac ataccacaat gggaaccttc | 9660 |
| aaaaggatgg aatgattggc aacaagtgcc tttctgttca caccacttcc accagctaat | 9720 |
| tatgaaggat gggagggaga tagtggtgcc atgccgcaac caagatgaac ttgtggggag | 9780 |
| ggccagagta tcacaaggcg ccggatggag cctgagagaa accgcatgcc taggcaagtc | 9840 |
| atatgcacaa atgtggcagc tgatgtattt ccacaggaga gacctgagac tggcggctaa | 9900 |
| cgctatttgt tcagccgttc cagttgattg ggtcccaacc agccgcacca cctggtcgat | 9960 |
| ccatgcccat caccaatgga tgacaacaga agacatgtta tcagtatgga atagggtctg | 10020 |
| gatagaggaa aacccatgga tggaggataa gactcatgtg tccagttggg aagaagttcc | 10080 |
| atacctagga aagagggaag atcagtggtg tggatccctg ataggcttaa cagcaagggc | 10140 |
| cacctgggcc actaatatac aagtggccat aaaccaagtg agaaggctca ttgggaatga | 10200 |
| gaattatcta gattacatga catcaatgaa gagattcaag aatgagagtg atcccgaagg | 10260 |
| ggcactctgg taagtcaaca cattcacaaa ataaaggaaa ataaaaaatc aaatgaggca | 10320 |
| agaagtcagg ccagattaag ccatagtacg gtaagagcta tgctgcctgt gagccccgtc | 10380 |
| caaggacgta aaatgaagtc aggccgaaag ccacggtttg agcaagccgt gctgcctgtg | 10440 |
| gctccatcgt ggggatgtaa aaacccggga ggctgcaacc catggaagct gtacgcatgg | 10500 |
| ggtagcagac tagtggttag aggagacccc tcccaagaca caacgcagca gcggggccca | 10560 |
| acaccagggg aagctgtacc ctggtggtaa ggactagagg ttagaggaga ccccccgcgt | 10620 |
| aacaataaac agcatattga cgctgggaga ccagagatcc tgctgtctct acagcatc | 10680 |
| attccaggca cagaacgcca gaaaatggaa tggtgctgtt gaatcaacag gttct | 10735 |

<210> SEQ ID NO 2
<211> LENGTH: 10723
<212> TYPE: DNA
<213> ORGANISM: Dengue virus

<400> SEQUENCE: 2

| | |
|---|---|
| agttgttagt ctacgtggac cgacaaagac agattctttg agggagctaa gctcaatgta | 60 |
| gttctaacag ttttttaatt agagagcaga tctctgatga taaccaacg gaaaaaggcg | 120 |
| aaaaacacgc ctttcaatat gctgaaacgc gagagaaacc gcgtgtcgac tgtgcaacag | 180 |
| ctgacaaaga gattctcact tggaatgctg cagggacgag gaccattaaa actgttcatg | 240 |
| gccctggtgg cgttccttcg tttcctaaca atcccaccaa cagcagggat attgaagaga | 300 |
| tggggaacaa ttaaaaaatc aaaagctatt aatgttttga gagggttcag gaagagatt | 360 |
| ggaaggatgc tgaacatctt gaataggaga cgcagatctg caggcatgat cattatgctg | 420 |
| attccaacag tgatggcgtt ccatttaacc acacgtaacg gagaaccaca catgatcgtc | 480 |
| agcagacaag agaaagggaa aagtcttctg tttaaaacag aggttggcgt gaacatgtgt | 540 |

| | |
|---|---|
| accctcatgg ccatggacct tggtgaattg tgtgaagaca caatcacgta caagtgtccc | 600 |
| cttctcaggc agaatgagcc agaagacata gactgttggt gcaactctac gtccacgtgg | 660 |
| gtaacttatg ggacgtgtac caccatggga aacatagaa gagaaaaaag atcagtggca | 720 |
| ctcgttccac atgtgcgaat gggactggag acacgaactg aaacatggat gtcatcagaa | 780 |
| ggggcctgga acatgtcca gagaattgaa acttggatct tgagacatcc aggcttcacc | 840 |
| atgatggcag caatcctggc atacaccata gaacgacac atttccaaag agccctgatt | 900 |
| ttcatcttac tgacagctgt cactccttca atgacaatgc gttgcatagg aatgtcaaat | 960 |
| agagactttg tggaagggt ttcaggagga agctgggttg acatagtctt agaacatgga | 1020 |
| agctgtgtga cgacgatggc aaaaaacaaa ccaacattgg attttgaact gataaaaaca | 1080 |
| gaagccaaac agcctgccac cctaaggaag tactgtatag aggcaaagct aaccaacaca | 1140 |
| acaacagaat ctcgctgccc aacacaaggg gaacccagcc taaatgaaga gcaggacaaa | 1200 |
| aggttcgtct gcaaacactc catggtagac agaggatggg gaaatggatg tggactattt | 1260 |
| ggaaagggag gcattgtgac ctgtgctatg ttcagatgca aaaagaacat ggaaggaaaa | 1320 |
| gttgtgcaac cagaaaactt ggaatacacc attgtgataa cacctcactc aggggaagag | 1380 |
| catgcagtcg gaaatgacac aggaaaacat ggcaaggaaa tcaaaataac accacagagt | 1440 |
| tccatcacag aagcagaatt gacaggttat ggcactgtca caatggagtg ctctccaaga | 1500 |
| acgggcctcg acttcaatga gatggtgttg ctgcagatgg aaaataaagc ttggctggtg | 1560 |
| cacaggcaat ggttcctaga cctgccgtta ccatggttgc ccggagcgga cacacaagag | 1620 |
| tcaaattgga tacagaagga gacattggtc actttcaaaa atccccatgc gaagaaacag | 1680 |
| gatgttgttg ttttaggatc ccaagaaggg gccatgcaca cagcacttac aggggccaca | 1740 |
| gaaatccaaa tgtcatcagg aaacttactc ttcacaggac atctcaagtg caggctgaga | 1800 |
| atggacaagc tacagctcaa ggaatgtca tactctatgt gcacaggaaa gtttaaagtt | 1860 |
| gtgaaggaaa tagcagaaac acaacatgga acaatagtta tcagagtgca atatgaaggg | 1920 |
| gacgctctc catgcaagat ccctttgag ataatggatt tggaaaaaag acatgtctta | 1980 |
| ggtcgcctga ttacagtcaa cccaattgtg acagaaaaag atagcccagt caacatagaa | 2040 |
| gcagaacctc catttggaga cagctacatc atcataggag tagagccggg acaactgaag | 2100 |
| ctcaactggt ttaagaaagg aagttctatc ggccaaatgt ttgagacaac aatgagggg | 2160 |
| gcgaagagaa tggccatttt aggtgacaca gcctgggatt ttggatcctt gggaggagtg | 2220 |
| tttacatcta taggaaaggc tctccaccaa gtctttggag caatctatgg agctgccttc | 2280 |
| agtgggggtt catggactat gaaaatcctc ataggagtca ttatcacatg gataggaatg | 2340 |
| aattcacgca gcacctcact gtctgtgaca ctagtattgg tgggaattgt gacactgtat | 2400 |
| ttgggagtca tggtgcaggc cgatagtggt tgcgttgtga ctggaaaaaa caaagaactg | 2460 |
| aaatgtggca gtgggatttt catcacagac aacgtgcaca catggacaga acaatacaaa | 2520 |
| ttccaaccag aatcccttc aaaactagct tcagctatcc agaaagccca tgaagaggac | 2580 |
| atttgtggaa tccgctcagt aacaagactg gagaatctga tgtggaaaca aataacacca | 2640 |
| gaattgaatc acattctatc agaaaatgag gtgaagttaa ctattatgac aggagacatc | 2700 |
| aaaggaatca tgcaggcagg aaaacgatct ctgcggcctc agcccactga gctgaagtat | 2760 |
| tcatggaaaa catggggcaa agcaaaaatg ctctctacag agtctcataa ccagaccttt | 2820 |
| ctcattgatg gccccgaaac agcagaatgc cccaacacaa atagagcttg gaattcgttg | 2880 |

```
gaagttgaag actatggctt tggagtattc accaccaata tatggctaaa attgaaagaa   2940
aaacaggatg tattctgcga ctcaaaactc atgtcagcgg ccataaaaga caacagagcc   3000
gtccatgccg atatgggtta ttggatagaa agtgcactca atgacacatg gaagatagag   3060
aaagcctctt tcattgaagt taaaaactgc cactggccaa atcacacac cctctggagc    3120
aatggagtgc tagaaagtga gatgataatt ccaaagaatc tcgctggacc agtgtctcaa   3180
cacaactata gaccaggcta ccatacacaa ataacaggac catggcatct aggtaagctt   3240
gagatggact ttgatttctg tgatggaaca acagtggtag tgactgagga ctgcggaaat   3300
agaggaccct ctttgagaac aaccactgcc tctggaaaac tcataacaga atggtgctgc   3360
cgatcttgca cattaccacc gctaagatac agaggtgagg atgggtgctg gtacgggatg   3420
gaaatcagac cattgaagga gaagaagag aatttggtca actccttggt cacagctgga    3480
catgggcagg tcgacaactt ttcactagga gtcttgggaa tggcattgtt cctggaggaa   3540
atgcttagga cccgagtagg aacgaaacat gcaatactac tagttgcagt ttcttttgtg   3600
acattgatca cagggaacat gtcctttaga gacctgggaa gagtgatggt tatggtaggc   3660
gccactatga cggatgacat aggtatgggc gtgacttatc ttgccctact agcagccttc   3720
aaagtcagac caactttggc agctggacta ctcttgagaa agctgaccte caaggaattg   3780
atgatgacta ctataggaat tgtactcctc tcccagagca ccataccaga gaccattctt   3840
gagttgactg atgcgttagc cttaggcatg atggtcctca aaatggtgag aaatatggaa   3900
aagtatcaat tggcagtgac tatcatggct atcttgtgcg tcccaaacgc agtgatatta   3960
caaaacgcat ggaaagtgag ttgcacaata ttggcagtgg tgtccgtttc cccactgttc   4020
ttaacatcct cacagcaaaa aacagattgg ataccattag cattgacgat caaaggtctc   4080
aatccaacag ctatttttct aacaaccctc tcaagaacca gcaagaaaag gagctggcca   4140
ttaaatgagg ctatcatggc agtcgggatg gtgagcattt tagccagttc tctcctaaaa   4200
aatgatattc ccatgacagg accattagtg gctggagggc tcctcactgt gtgctacgtg   4260
ctcactggac gatcggccga tttggaactg gagagagcag ccgatgtcaa atggaagac    4320
caggcagaga tatcaggaag cagtccaatc ctgtcaataa caatatcaga agatggtagc   4380
atgtcgataa aaaatgaaga ggaagaacaa acactgacca tactcattag aacaggattg   4440
ctggtgatct caggactttt tcctgtatca ataccaatca cggcagcagc atggtacctg   4500
tgggaagtga agaaacaacg ggccggagta ttgtgggatg ttccttcacc cccacccatg   4560
ggaaaggctg aactggaaga tggagcctat agaattaagc aaaaagggat tcttggatat   4620
tcccagatcg gagccggagt ttacaaagaa ggaacattcc atacaatgtg gcatgtcaca   4680
cgtggcgctg ttcctaatgca taaaggaaag aggattgaac caacatgggc ggacgtcaag   4740
aaagacctaa tatcatatgg aggaggctgg aagttagaag gagaatggaa ggaaggagaa   4800
gaagtccagg tattggcact ggagcctgga aaaaatccaa gagccgtcca aacgaaacct   4860
ggtctttca aaaccaacgc cggaacaata ggtgctgtat ctctggactt ttctcctgga   4920
acgtcaggat ctccaattat cgacaaaaaa ggaaagttg tgggtcttta tggtaatggt   4980
gttgttacaa ggagtggagc atatgtgagt gctatagccc agactgaaaa aagcattgaa   5040
gacaacccag atcgaagaa tcacatttt cgaaagagaa gactgaccat catggaccte   5100
caccccaggag cgggaaagac gaagagatac cttccggcca tagtcagaga agctataaaa  5160
cggggtttga gaacattaat cttggcccc actagagttg tggcagctga aatggaggaa   5220
gccccttagag gacttccaat aagataccag accccagcca tcagagctga gcacaccggg  5280
```

```
cgggagattg tggacctaat gtgtcatgcc acatttacca tgaggctgct atcaccagtt    5340
agagtgccaa actacaacct gattatcatg gacgaagccc atttcacaga cccagcaagt    5400
atagcagcta gaggatacat ctcaactcga gtggagatgg gtgaggcagc tgggattttt    5460
atgacagcca ctcccccggg aagcagagac ccatttcctc agagcaatgc accaatcata    5520
gatgaagaaa gagaaatccc tgaacgctcg tggaattccg gacatgaatg ggtcacggat    5580
tttaaaggga agactgtttg gttcgttcca agtataaaag caggaaatga tatagcagct    5640
tgcctgagga aaaatggaaa gaaagtgata caactcagta ggaagacctt tgattctgag    5700
tatgtcaaga ctagaaccaa tgattgggac ttcgtggtta caactgacat ttcagaaatg    5760
ggtgccaatt tcaaggctga gagggttata gaccccagac gctgcatgaa accagtcata    5820
ctaacagatg gtgaagagcg ggtgattctg gcaggaccta tgccagtgac ccactctagt    5880
gcagcacaaa aagagggag aataggaaga atccaaaaa atgagaatga ccagtacata    5940
tacatggggg aacctctgga aaatgatgaa gactgtgcac actggaaaga agctaaaatg    6000
ctcctagata acatcaacac gccagaagga atcattccta gcatgttcga accagagcgt    6060
gaaaaggtgg atgccattga tggcgaatac cgcttgagag gagaagcaag gaaaaccttt    6120
gtagacttaa tgagaagagg agacctacca gtctggttgg cctacagagt ggcagctgaa    6180
ggcatcaact acgcagacag aaggtggtgt tttgatggag tcaagaacaa ccaaatccta    6240
gaagaaaacg tggaagttga aatctggaca aaagaagggg aaaggaagaa attgaaaccc    6300
agatggttgg atgctaggat ctattctgac ccactggcgc taaaagaatt taaggaattt    6360
gcagccggaa gaaagtctct gacccctgaac ctaatcacag aaatgggtag gctcccaacc    6420
ttcatgactc agaaggcaag agacgcactg gacaacttag cagtgctgca cacggctgag    6480
gcaggtggaa gggcgtacaa ccatgctctc agtgaactgc cggagaccct ggagacattg    6540
cttttactga cacttctggc tacagtcacg ggagggatct ttttattctt gatgagcgca    6600 agggggcatag ggaagatgac cctgggaatg tgctgcataa tcacggctag catcctccta    6660
tggtacgcac aaatacagcc acactggata gcagcttcaa taatactgga gttttttctc    6720
atagttttgc ttattccaga acctgaaaaa cagagaacac cccaagacaa ccaactgacc    6780
tacgttgtca tagccatcct cacagtggtg gccgcaacca tggcaaacga gatgggtttc    6840
ctagaaaaaa cgaagaaaga tctcggattg ggaagcattg caacccagca acccgagagc    6900
aacatcctgg acatagatct acgtcctgca tcagcatgga cgctgtatgc cgtggccaca    6960
acatttgtta caccaatgtt gagacatagc attgaaaatt cctcagtgaa tgtgtcccta    7020
acagctatag ccaaccaagc cacagtgtta atgggtctcg ggaaaggatg gccattgtca    7080
aagatggaca tcggagttcc ccttctcgcc attggatgct actcacaagt caaccccata    7140
actctcacag cagctcttttt cttattggta gcacattatg ccatcatagg gccaggactc    7200
caagcaaaag caaccagaga agctcagaaa agagcagcgg cgggcatcat gaaaaaccca    7260
actgtcgatg gaataacagt gattgaccta gatccaatac cttatgatcc aaagtttgaa    7320
aagcagttgg gacaagtaat gctcctagtc ctctgcgtga ctcaagtatt gatgatgagg    7380
actacatggg ctctgtgtga ggctttaacc ttagctaccg gccccatctc cacattgtgg    7440
gaaggaaatc cagggaggtt ttggaacact accattgcgg tgtcaatggc taacattttt    7500
agagggagtt acttggccgg agctggactt ctcttttcta ttatgaagaa cacaaccaac    7560
acaagaaggg gaactggcaa cataggagag acgcttggag agaaatggaa aagccgattg    7620
```

```
aacgcattgg gaaaaagtga attccagatc tacaagaaaa gtggaatcca ggaagtggat    7680
agaaccttag caaagaagg cattaaaaga ggagaaacgg accatcacgc tgtgtcgcga    7740
ggctcagcaa aactgagatg gttcgttgag agaaacatgg tcacaccaga agggaaagta    7800
gtggacctcg gttgtggcag aggaggctgg tcatactatt gtggaggact aaagaatgta    7860
agagaagtca aaggcctaac aaaaggagga ccaggacacg aagaacccat ccccatgtca    7920
acatatgggt ggaatctagt gcgtcttcaa agtggagttg acgttttctt catcccgcca    7980
gaaaagtgtg acacattatt gtgtgacata ggggagtcat caccaaatcc cacagtggaa    8040
gcaggacgaa cactcagagt ccttaactta gtagaaaatt ggttgaacaa caacactcaa    8100
ttttgcataa aggttctcaa cccatatatg ccctcagtca tagaaaaaat ggaagcacta    8160
caaaggaaat atggaggagc cttagtgagg aatccactct cacgaaactc cacacatgag    8220
atgtactggg tatccaatgc ttccgggaac atagtgtcat cagtgaacat gatttcaagg    8280
atgttgatca acagatttac aatgagatac aagaaagcca cttacgagcc ggatgttgac    8340
ctcggaagcg gaacccgtaa catcgggatt gaaagtgaga taccaaacct agatataatt    8400
gggaaaagaa tagaaaaaat aaagcaagag catgaaacat catggcacta tgaccaagac    8460
cacccataca aaacgtgggc ataccatggt agctatgaaa caaaacagac tggatcagca    8520
tcatccatgg tcaacggagt ggtcaggctg ctgacaaaac cttgggacgt tgtcccatg    8580
gtgacacaga tggcaatgac agcacgact ccatttggac aacagcgcgt ttttaaagag    8640
aaagtggaca cgagaaccca agaaccgaaa gaaggcacga agaaactaat gaaaataaca    8700
gcagagtggc tttggaaaga attagggaag aaaagacac ccaggatgtg caccagagaa    8760
gaattcacaa gaaaggtgag aagcaatgca gccttggggg ccatattcac tgatgagaac    8820
aagtggaagt cggcacgtga ggctgttgaa gatagtaggt tttgggagct ggttgacaag    8880
gaaaggaatc tccatcttga aggaaagtgt gaaacatgtg tgtacaacat gatgggaaaa    8940
agagagaaga agctagggga attcggcaag gcaaaaggca gcagagccat atggtacatg    9000
tggcttggag cacgcttctt agagtttgaa gccctaggat tcttaaatga agatcactgg    9060
ttctccagag agaactccct gagtggagtg aaggagaag ggctgcacaa gctaggttac    9120
attctaagag acgtgagcaa aaaagaggga ggagcaatgt atgccgatga caccgcagga    9180
tgggatacaa aaatcacact agaagaccta aaaaatgaag agatggtaac aaaccacatg    9240
gaaggagaac acaagaaact agccgaggcc attttcaaac taacgtacca aaacaaggtg    9300
gtgcgtgtgc aaagaccaac accaagaggc acagtaatgg acatcatatc gagaagagac    9360
caaagaggta gtggacaagt tggcacctat ggactcaata ctttcaccaa tatggaagcc    9420
caactaatca gacagatgga gggagaagga gtctttaaaa gcattcagca cctaacaatc    9480
acagaagaaa tcgctgtgca aaactggtta gcaagagtgg ggcgcgaaag gttatcaaga    9540
atggccatca gtgagatga ttgtgttgtg aaacctttag atgacaggtt cgcaagcgct    9600
ttaacagctc taaatgacat gggaaagatt aggaaagaca tacaacaatg ggaaccttca    9660
agaggatgga atgattggac acaagtgccc ttctgttcac accatttcca tgagttaatc    9720
atgaaagacg tcgcgtact cgttgttcca tgtagaaacc aagatgaact gattggcaga    9780
gcccgaatct cccaaggagc agggtggtct ttgcgggaga cggcctgttt ggggaagtct    9840
tacgcccaaa tgtggagctt gatgtacttc cacagacgcg acctcaggct ggcggcaaat    9900
gctatttgct cggcagtacc atcacattgg gttccaacaa gtcgaacaac ctggtccata    9960
catgctaaac atgaatggat gacaacggaa gacatgctga cagtctggaa cagggtgtgg    10020
```

```
attcaagaaa  acccatggat  ggaagacaaa  actccagtgg  aaacatggga  ggaaatccca    10080 tacttggga   aaagagaaga  ccaatggtgc  ggctcattga  ttgggttaac  aagcagggcc    10140
acctgggcaa  agaacatcca  agcagcaata  aatcaagtta  gatcccttat  aggcaatgaa    10200
gaatacacag  attacatgcc  atccatgaaa  agattcagaa  gagaagagga  agaagcagga    10260
gttctgtggt  agaaagcaaa  actaacatga  aacaaggcta  gaagtcaggt  cggattaagc    10320
catagtacgg  aaaaaactat  gctacctgtg  agccccgtcc  aaggacgtta  aaagaagtca    10380
ggccatcata  aatgccatag  cttgagtaaa  ctatgcagcc  tgtagctcca  cctgagaagg    10440
tgtaaaaaat  ccgggaggcc  acaaaccatg  gaagctgtac  gcatggcgta  gtggactagc    10500
ggttagggga  gacccctccc  ttacaaatcg  cagcaacaat  gggggcccaa  ggcgagatga    10560
agctgtagtc  tcgctggaag  gactagaggt  tagaggagac  cccccgaaa   caaaaaacag    10620 catattgacg  ctgggaaaga  ccagagatcc  tgctgtctcc  tcagcatcat  tccaggcaca    10680
gaacgccaga  aaatggaatg  gtgctgttga  atcaacaggt  tct                       10723
```